US006211183B1

(12) United States Patent
Marlowe et al.

(10) Patent No.: US 6,211,183 B1
(45) Date of Patent: Apr. 3, 2001

(54) SELECTIVE FACTOR XA INHIBITORS

(75) Inventors: Charles K. Marlowe; Bing-Yan Zhu; Robert M. Scarborough, all of Belmont, CA (US)

(73) Assignee: COR Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 09/058,564

(22) Filed: Apr. 13, 1998

Related U.S. Application Data

(60) Provisional application No. 60/069,884, filed on Apr. 14, 1997.

(51) Int. Cl.$^7$ .................. A61K 31/69; A61K 31/495; A61P 7/02; C07D 241/02; C07D 403/00
(52) U.S. Cl. .................. 514/255.02; 514/64; 514/252.18; 514/253.01; 514/253.05; 514/253.07; 514/253.09; 514/253.1; 514/254.04; 544/229; 544/295; 544/357; 544/360; 544/363; 544/364; 544/367; 544/368; 544/369; 544/384; 544/385
(58) Field of Search .................. 514/64, 252.18, 514/253.01, 253.05, 253.07, 253.09, 253.1, 254.04, 255.02; 544/229, 295, 357, 360, 363, 364, 367, 368, 369, 384, 385

(56) References Cited

U.S. PATENT DOCUMENTS

| | | | |
|---|---|---|---|
| 3,352,866 | * 11/1967 | Dornfeld | 260/268 |
| 3,845,046 | * 10/1974 | Fauran et al. | 260/247.5 |
| 4,178,438 | * 12/1979 | Haase et al. | 536/30 |
| 4,720,493 | * 1/1988 | Kawakita et al. | 514/230 |
| 5,028,610 | * 7/1991 | Hirai et al. | 514/259 |
| 5,194,614 | * 3/1993 | Andrieux et al. | 544/400 |
| 5,276,051 | * 1/1994 | Lesieur et al. | 514/415 |
| 5,443,815 | 8/1995 | Dean et al. | 424/1.41 |
| 5,492,895 | 2/1996 | Vlasuk et al. | 514/18 |
| 5,521,179 | 5/1996 | Bernstein et al. | 514/235.5 |
| 5,563,136 | 10/1996 | Capet et al. | 514/221 |
| 5,583,146 | 12/1996 | Kimball et al. | 514/326 |
| 5,612,363 | 3/1997 | Mohan et al. | 514/392 |
| 5,618,811 | 4/1997 | Lowe, III | 514/218 |
| 5,632,898 | * 5/1997 | Jung et al. | 210/656 |
| 5,668,289 | 9/1997 | Sanderson et al. | 546/293 |
| 5,703,208 | 12/1997 | Semple et al. | 530/331 |
| 5,714,499 | 2/1998 | Semple et al. | 514/316 |
| 5,721,214 | 2/1998 | Marlowe et al. | 514/18 |
| 5,776,902 | 7/1998 | Bachovchin | 514/18 |
| 5,861,509 | * 1/1999 | Schnorrenberg et al. | 544/130 |
| 5,948,785 | 9/1999 | Akahoshi et al. | 514/269 |

FOREIGN PATENT DOCUMENTS

| | | |
|---|---|---|
| 0 167 919 | 1/1986 | (EP) . |
| 0 239 461 | * 9/1987 | (EP) . |
| 0 471 651 | 2/1992 | (EP) . |
| 0 512 831 | 11/1992 | (EP) . |
| 0 529 858 | 3/1993 | (EP) . |
| 0 761 220 | 3/1997 | (EP) . |
| 0 765 873 | 4/1997 | (EP) . |
| 53-034735 | * 3/1978 | (JP) . |
| 58-096075 | * 6/1983 | (JP) . |
| 58-194873 | * 11/1983 | (JP) . |
| 58-216170 | * 12/1983 | (JP) . |
| 2-083375 | * 3/1990 | (JP) . |
| 3-148223 | * 6/1991 | (JP) . |
| 5-241287 | * 9/1993 | (JP) . |
| WO 94/13648 | 6/1994 | (WO) . |
| WO 93/21213 | 10/1995 | (WO) . |
| WO 95/28399 | 10/1995 | (WO) . |
| 95/35311 | 12/1995 | (WO) . |
| 96/18644 | 6/1996 | (WO) . |
| 96/31214 | 10/1996 | (WO) . |
| 96/40653 | 12/1996 | (WO) . |
| 97/01338 | 1/1997 | (WO) . |
| 97/05160 | 2/1997 | (WO) . |
| 97/14417 | 4/1997 | (WO) . |
| 97/17363 | 5/1997 | (WO) . |
| 97/30073 | 8/1997 | (WO) . |
| 98/16523 | 4/1998 | (WO) . |
| 98/16547 | 4/1998 | (WO) . |
| 99/07731 | 2/1999 | (WO) . |
| 99/07732 | 2/1999 | (WO) . |

OTHER PUBLICATIONS

R. Tomatis, et al., "Synthesis and pharmacological activity of Leu–Enkephalins modified at Gly $^2$–Gly $^3$ nitrogens," *European Journal of Medicinal Chemistry—Chimica Therapeutica*, vol. 16, No. 3, pp. 229–232 (1981).

Gennaro, et al., Eds., Remington: The Science and Practice of Pharmacy, Mack Printing Company, Easton, Pennsylvania (1995).

Kaiser et al., Factor Xa Inhibitors as Novel Antithrombotic Agents: Facts and Perspectives, *Cardiovascular Drug Reviews*, 12(3):225–236 (1994).

Robl, et al., Dual Metalloprotease Inhibitors. II. Effect of Substitution and Stereochemistry on Benzazepinone Based Mercaptoacetyls, *Bioorganic and Medicinal Chemistry Letters* 4(15):1795–1800 (1994).

Robl, et al., Dual Metalloprotease Inhibitors. 6. Incorporation of Bicyclic and Substituted Monocyclic Azepinones as Dipeptide Surrogates in Angiotensin–Converting Enzyme/Neutral Endopeptidase Inhibitors, *Journal of Medicinal Chemistry*, 39(2):494–502 (1996).

Semple, et al., Design, Synthesis, and Evolution of a Novel, Selective, and Orally Bioavailable Class of Thrombin Inhibitors: P1–arginnal derivatives incorporating P3–4 lactam sulfonamide moieties , *J. Med. Chem.* 39:4531–4536 (1996).

Skiles, et al., *Bioorganic & Medicinal Chemistry Letters*, 3(4):773–778 (1993).

Skiles, et al., Chemical Abstracts, vol. 120, No. 11, (1994) (CA: 120:135101a).

Szelke, et al., Chemical Abstracts, 97:624 (1982) (CA: 97:39405p).

Tourwé, et al., Conformational Restriction of Tyr and Phe Side Chains in Opioid Peptides: Information About Preferred and Bioactive Side–Chain Topology, *Biopolymers* 38:1–12 (1996).

\* cited by examiner

*Primary Examiner*—Richard L. Raymond
*Assistant Examiner*—Brenda Coleman
(74) *Attorney, Agent, or Firm*—Morgan, Lewis & Bockius LLP

(57) ABSTRACT

Novel compounds, their salts and compositions related thereto having activity against mammalian factor Xa are disclosed. The compounds are useful in vitro or in vivo for preventing or treating coagulation disorders.

20 Claims, No Drawings

SELECTIVE FACTOR XA INHIBITORS

This application claims priority of copending provisional application(s) No. 60/069,884 filed on Apr. 14, 1997.

FIELD OF THE INVENTION

This invention relates to a novel class of cyclic diaza compounds which are potent and highly selective inhibitors of factor Xa or factor Xa when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin).

BACKGROUND OF THE INVENTION

Blood coagulation protects mammalian species when the integrity of the blood vessel wall is damaged and uncontrolled loss of blood threatens survival. Coagulation, resulting in the clotting of blood, is an important component of hemostasis. Under normal hemostatic circumstances, there is maintained an acute balance of clot formation and clot removal (fibrinolysis). The blood coagulation cascade involves the conversion of a variety of inactive enzymes (zymogens) into active enzymes, which ultimately convert the soluble plasma protein fibrinogen into an insoluble matrix of highly cross-linked fibrin. (See Davie, et al., "The Coagulation Cascade: Initiation, Maintenance and Regulation" *Biochemistry* 30:10363–10370 (1991)). Blood platelets which adhere to damaged blood vessels are activated and incorporated into the clot and thus play a major role in the initial formation and stabilization of hemostatic "plugs". In certain diseases of the cardiovascular system, deviations from normal hemostasis push the balance of clot formation and clot dissolution towards life-threatening thrombus formation when thrombi occlude blood flow in coronary vessels (myocardial infarctions) or limb and pulmonary veins (venous thrombosis). Although platelets and blood coagulation are both involved in thrombus formation, certain components of the coagulation cascade are primarily responsible for the amplification or acceleration of the processes involved in platelet aggregation and fibrin deposition.

A key enzyme in the coagulation cascade, as well as in hemostasis, is thrombin. Thrombin is intimately involved in the process of thrombus formation, but under normal circumstances can also play an anticoagulant role in hemostasis through its ability to convert protein C into activated protein C in a thrombomodulin-dependent manner. Thrombin plays a central role in thrombosis through its ability to catalyze the penultimate conversion of fibrinogen into fibrin and through its potent platelet activation activity. Direct or indirect inhibition of thrombin activity has been the focus of a variety of recent anticoagulant strategies as reviewed by Claeson "Synthetic Peptides and Peptidomimetics as Substrates and Inhibitors of Thrombin and Other Proteases in the Blood Coagulation System", *Blood Coag. Fibrinol.* 5:411–436 (1994). The major classes of anticoagulants currently used in the clinic directly or indirectly affect thrombin (i.e. heparins, low-molecular weight heparins and coumarins). Thrombin is generated at the convergence of the intrinsic and extrinsic coagulation pathways by the prothrombinase complex. The prothrombinase complex is formed when activated Factor X (factor Xa) and its non-enzymatic cofactor, factor Va assemble on phospholipid surfaces in a $Ca^{-2}$-dependent fashion as reviewed by Mann, et al., "Surface-Dependent Reactions of the Vitamin K-Dependent Enzymes", *Blood* 76:1–16 (1990). The prothrombinase complex converts the zymogen prothrombin into the active procoagulant thrombin.

The location of the prothrombinase complex at the convergence of the intrinsic and extrinsic coagulation pathways, and the significant amplification of thrombin generation (393,000-fold over uncomplexed factor Xa) mediated by the complex at a limited number of targeted catalytic units present at vascular lesion sites, suggests that inhibition of thrombin generation is an ideal method to block uncontrolled procoagulant activity. Unlike thrombin, which acts on a variety of protein substrates as well as at a specific receptor, factor Xa appears to have a single physiologic substrate, namely prothrombin.

Plasma contains an endogenous inhibitor of both the factor VIIa-tissue factor (TF) complex and factor Xa called tissue factor pathway inhibitor (TFPI). TFPI is a Kunitz-type protease inhibitor with three tandem Kunitz domains. TFPI inhibits the TF/fVIIa complex in a two-step mechanism which includes the initial interaction of the second Kunitz domain of TFPI with the active site of factor Xa, thereby inhibiting the proteolytic activity of factor Xa. The second step involves the inhibition of the TF/fVIIa complex by formation of a quaternary complex TF/fVIIa/TFPI/fXa as described by Girard, et al., "Functional Significance of the Kunitz-type Inhibitory Domains of Lipoprotein-associated Coagulation Inhibitor", *Nature* 338:518–520 (1989).

Polypeptides derived from hematophagous organisms have been reported which are highly potent and specific inhibitors of factor Xa. U.S. Pat. No. 4,588,587 awarded to Gasic, describes anticoagulant activity in the saliva of the Mexican leech, *Haementeria officinalis*. A principal component of this saliva is shown to be the polypeptide factor Xa inhibitor, antistasin, by Nutt, et al, "The Amino Acid Sequence of Antistasin, a Potent Inhibitor of Factor Xa Reveals a Repeated Internal Structure", *J. Biol. Chem.* 263:10162–10167 (1988).

Another potent and highly specific inhibitor of Factor Xa, tick anticoagulant peptide, has been isolated from the whole body extract of the soft tick *Ornithidoros moubata*, as reported by Waxman, et al., "Tick Anticoagulant Peptide (TAP) is a Novel Inhibitor of Blood Coagulation Factor Xa", *Science* 248:593–596 (1990).

Other polypeptide type inhibitors of factor Xa have been reported including the following citations by: Condra, et al, "Isolation and Structural Characterization of a Potent Inhibitor of Coagulation Factor Xa from the Leech *Haementeria ghilianii*", *Thromb. Haemost.* 61:437–441 (1989); Blankenship, et al., "Amino Acid Sequence of Ghilanten: Anti-coagulant-antimetastatic Principle of the South American Leech, *Haementeria ghilianit*", *Biochem. Biophys. Res. Commun.* 166:1384–1389 (1990); Brankamp, et al., "Ghilantens: Anticoagulants, Antimetastatic Proteins from the South American Leech *Haementeria ghilianii*", *J. Lab. Clin. Med.* 115:89–97 (1990); Jacobs, et al., "Isolation and Characterization of a Coagulation Factor Xa Inhibitor from Black Fly Salivary Glands", *Thromb. Haemost.* 64:235–238 (1990); Rigbi, et al., "Bovine Factor Xa Inhibiting Factor and Pharmaceutical Compositions Containing the Same", European Patent Application, 352,903 (1990); Cox, "Coagulation Factor X Inhibitor From the Hundred-pace Snake *Deinagkistrodon acutus* venom", *Toxicon* 31:1445–1457 (1993); Cappello, et al., "Ancylostoma Factor Xa Inhibitor: Partial Purification and its Identification as a Major Hookworm-derived Anticoagulant In Vitro", *J. Infect. Dis.* 167:1474–1477 (1993); Seymour, et al., "Ecotin is a Potent Anticoagulant and Reversible Tight-binding Inhibitor of Factor Xa", *Biochemistry* 33:3949–3958 (1994).

Factor Xa inhibitory compounds which are not large polypeptide-type inhibitors have also been reported including: Tidwell, et al, "Strategies for Anticoagulation With Synthetic Protease Inhibitors. Xa Inhibitors Versus Thrombin Inhibitors", *Thromb. Res.* 19:339–349 (1980); Turner, et al, "p-Amidino Esters as Irreversible Inhibitors of Factor IXa and Xa and Thrombin", *Biochemistry* 25:4929–4935 (1986); Hitomi, et al., "Inhibitory Effect of New Synthetic Protease Inhibitor (FUT-175) on the Coagulation System", *Haemostasis* 15:164–168 (1985); Sturzebecher, et al., "Synthetic Inhibitors of Bovine Factor Xa and Thrombin. Comparison of Their Anticoagulant Efficiency", *Thromb. Res.* 54:245–252 (1989); Kam, et al, "Mechanism Based Isocoumarin Inhibitors for Trypsin and Blood Coagulation Serine Proteases: New Anticoagulants", *Biochemistry* 27:2547–2557 (1988); Hauptmann, et al., "Comparison of the Anticoagulant and Antithrombotic Effects of Synthetic Thrombin and Factor Xa Inhibitors", *Thromb. Haemost.* 63:220–223 (1990); Miyadera, et al., Japanese Patent Application JP 6327488 (1994); Nagahara, et al., "Dibasic (Amidinoaryl)propanoic Acid Derivatives as Novel Blood Coagulation Factor Xa Inhibitors", *J. Med. Chem.* 37:1200–1207 (1994); Vlasuk, et al., "Inhibitors of Thrombosis" WO 93/15756; and Brunck, et al., "Novel Inhibitors of Factor Xa", WO 94/13693. Al-obeidi, et al., "Factor Xa Inhibitors", WO 95/29189, discloses pentapeptide X1-Y-I-R-X2 derivatives as factor Xa inhibitors. Said compounds are useful for inhibiting blood clotting in the treatment of thrombosis, stroke, and myocardial infarction.

SUMMARY OF THE INVENTION

The present invention relates to novel peptide mimetic analogs, their pharmaceutically acceptable isomers, salts, hydrates, solvates and prodrug derivatives.

In another aspect, the present invention includes pharmaceutical compositions comprising a pharmaceutically effective amount of the compounds of this invention and a pharmaceutically acceptable carrier. These compositions are useful as potent and specific inhibitors of blood coagulation in mammals.

In yet another aspect, the invention relates to methods of using these inhibitors as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. These compositions may optionally include anticoagulants, antiplatelet agents, and thrombolytic agents.

In other aspects of the invention compounds are provided which are useful as diagnostic reagents.

In preferred embodiments, the present invention provides compounds of general formula I:

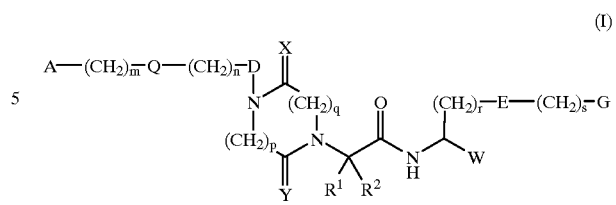

(I)

Wherein:

$R^1$ is selected from the group consisting of H, $C_{1-6}$alkyl, $C_{3-8}$cycloalkyl, $C_{1-3}$alkylaryl, $C_{1-3}$alkyl-$C_{3-8}$-cycloalkyl and aryl and $R^2$ is H, or $R^1$ and $R^2$ are taken together to form a carbocyclic ring;

m is an integer from 0–2;

n is an integer from 0–6;

p is an integer from 0–2;

q is an integer from 1–3;

r is an integer from 0–4;

s is an integer from 0–1;

A is selected from the group consisting of $R^3$, —$NR^3R^4$,

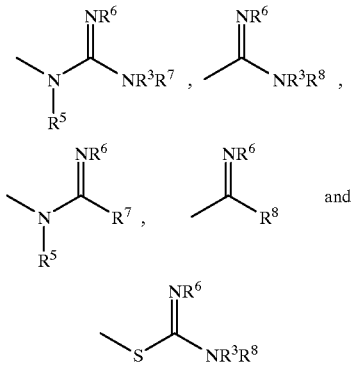

where $R^3$, $R^4$, $R^5$ and $R^6$ are independently selected from the group consisting of H, —OH, $C_{1-6}$alkyl, aryl and $C_{1-4}$alkylaryl; $R^7$ is selected from the group consisting of H, $C_{1-6}$alkyl, aryl and $C_{1-4}$alkylaryl, or can be taken together with $R^5$ or $R^6$ to form a 5–6 membered ring; and $R^8$ is selected from the group consisting of H, $C_{1-6}$alkyl, aryl and $C_{1-4}$alkylaryl, or can be taken together with $R^6$ to form a 5–6 membered ring;

Q is selected from the group consisting of a direct link, $C_{1-6}$alkyl, $C_{3-8}$cycloalkyl, $C_{2-6}$alkenyl, $C_{2-6}$alkenylaryl, aryl, and a five to ten membered heterocyclic ring system containing 1–4 heteroatoms selected from the group consisting of N, O and S;

D is selected from the group consisting of a direct link, —CO—, —$SO_2$—, —O—CO—, —$NR^9$—$SO_2$— and —$NR^9$—CO—, where $R^9$ is selected from the group consisting of H, —OH, $C_{1-6}$alkyl, aryl and $C_{1-4}$alkylaryl;

E is selected from the group consisting of a direct link, $C_{3-4}$Cycloaklyl, aryl, and a five to ten membered heterocyclic ring system containing 1–4 heteroatoms selected from the group consisting of N, O and S;

G is selected from the group consisting of $R^{10}$, —$NR^{40}OR^{11}$,

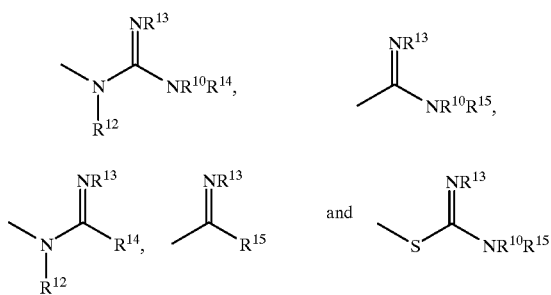

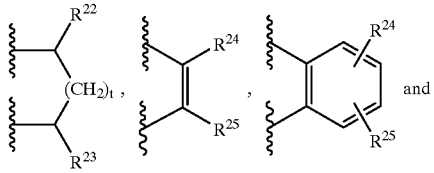

L is selected from the group consisting of:

where $R^{10}$, $R^{11}$, $R^{12}$ and $R^{13}$ are independently selected from the group consisting of H, —OH, $C_{1-6}$alkyl, aryl and $C_{1-4}$alkylaryl; $R^{14}$ is selected from the group consisting of H, $C_{1-6}$alkyl, aryl and $C_{1-4}$alkylaryl, or can be taken together with $R^{12}$ or $R^{13}$ to form a 5–6 membered ring; and $R^{15}$ is selected from the group consisting of H, $C_{1-6}$alkyl, aryl and $C_{1-4}$alkylaryl, or can be taken together with $R^{13}$ to form a 5–6 membered ring; with the proviso that when G is $R^{10}$, then E must contain at least one N atom;

X and Y are independently selected from the group consisting of 0 and $H_2$;

W is selected from the group consisting of H.

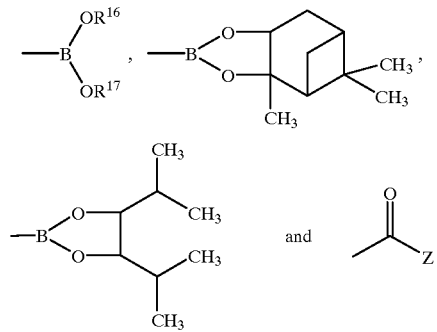

where $R^{16}$ and $R^{17}$ are independently selected from the group consisting of H, $C_{1-3}$alkyl and aryl; and Z is selected from the group consisting of H, —$COOR^{18}$, —$CONR^{18}R^{19}$, —$CF_3$, —$CF_2CF_3$ and a group having the formula

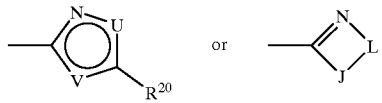

where:

$R^{18}$ and $R^{19}$ are independently selected from the group consisting of H, $C_{1-6}$alkyl, aryl and $C_{1-4}$alkylaryl;

U is selected from the group consisting of —O—, —S—, —N— and —NH—; and

V is selected from the group consisting of —O—, —S—, —N— and —NH—; with the proviso that at least one of U or V is —N— or —NH—;

$R^{20}$ is selected from the group consisting of H, $C_{1-6}$alkyl, $C_{2-6}$-alkenyl, $C_{0-6}$alkylaryl, $C_{2-6}$alkenylaryl, $C_{0-6}$alkylheterocyclo, $C_{2-6}$alkenylheterocyclo, —$CF_3$ and —$CF_2CF_3$;

J is selected from the group consisting of —S—, —SO—, —$SO_2$—, —O— and —$NR^{21}$—, where $R^{21}$ is selected from the group consisting of H, $C_{1-6}$alkyl and benzyl; and a $C_{6-10}$ heterocyclic ring system substituted by $R^{24}$ and $R^{25}$ and containing 1–4 heteroatoms selected from N, S and O; where t is an integer from 0–2;

$R^{22}$ and $R^{23}$ are independently selected from the group consisting of H, $C_{1-6}$alkyl, aryl, $C_{1-6}$alkylaryl, —$COOR^{26}$, —$CONR^{26}R^{27}$, —CN and —$CF_3$;

$R^{24}$ and $R^{25}$ are independently selected from the group consisting of H, $C_{1-6}$alkyl, aryl, $C_{1-6}$alkylaryl, $C_{1-4}$alkyloxy, halogen, —$NO_2$, —$NR^{26}R^{27}$, —$NR^{26}COR^{27}$, —$OR^{26}$, —$OCOR^{26}$, —$COOR^{26}$, —$CONR^{26}R^{27}$, —CN, —$CF_3$, —$SO_2NR^{26}R^{27}$ and $C_{1-6}$alkyl-$OR^{26}$; and $R^{26}$ and $R^{27}$ are independently selected from the group consisting of H, $C_{1-6}$alkyl, $C_{1-3}$alkylaryl and aryl; and all pharmaceutically acceptable salts and optical isomers thereof.

DETAILED DESCRIPTION OF THE INVENTION DEFINITIONS

In accordance with the present invention and as used herein, the following terms are defined with the following meanings, unless explicitly stated otherwise.

The term "alkyl" refers to saturated aliphatic groups including straight-chain, branched-chain, cyclic groups, and combinations thereof, having the number of carbon atoms specified, or if no number is specified, having up to 12 carbon atoms. The term "cycloalkyl" refers to a mono-, bi-, or tricyclic aliphatic ring having 3 to 12 carbon atoms, preferably 3 to 7 carbon atoms.

The term "alkenyl" refers to unsaturated aliphatic groups including straight-chain, branched-chain, cyclic groups, and combinations thereof, having at least one double bond and having the number of carbon atoms specified.

The term "aryl" refers to an unsubstituted or substituted aromatic ring(s), substituted with one, two or three substituents such as, by way of example and not limitation, $C_{1-6}$alkoxy, $C_{1-6}$alkyl, $C_{1-6}$alkylamino, hydroxy, halogen, cyano (—CN), mercapto, nitro (—$NO_2$), thioalkoxy, carboxaldehyde, carboxyl, carboalkoxy, carboxamide, —NR'R", —NR'COR", —OR, —OCOR, —COOR, —CONR'R", —$CF_3$, —$SO_2$NR'R" and $C_{1-6}$alkyl—OR; aryl, $C_{1-6}$alkylaryl (where the R groups can be H, $C_{1-6}$alkyl, $C_{1-3}$alkylaryl and aryl), including but not limited to carbocyclic aryl, heterocyclic aryl, biaryl and triaryl groups and the like, all of which may be optionally substituted. Preferred aryl groups include phenyl, halophenyl, $C_{1-6}$ alkylphenyl, naphthyl, biphenyl phenanthrenyl, naphthacenyl, and aromatic heterocyclics or heteroaryls, the latter of which is an aryl group containing one to four heteroatoms selected from the group consisting of nitrogen, oxygen and sulfur. Aryl groups preferably have 5–14 carbon atoms making up the ring(s) structure, while heteroaryls preferably have 1–4 heteroatoms, with the remaining 4–10 atoms being carbon atoms.

The terms "heterocyclo" and "hetero cyclic ring system" as used herein refers to any saturated or unsaturated mono- or bicyclic ring system, containing from one to four heteroatoms, selected from the group consisting of nitrogen, oxygen and sulfur. Typical examples of monocyclic ring systems include piperidinyl, pyrrolidinyl, pyridinyl, piperidonyl, pyrrolidonyl and thiazolyl, while examples of bicyclic ring systems include benzimidazolyl, benzothiazolyl and benzoxazolyl, all of which may be substituted.

The term "carbocyclic ring" as used herein refers to any saturated or unsaturated ring containing from three to six carbon atoms.

The terms "alkylaryl" and "alkenylaryl" as used herein refer to an alkyl group or alkenyl group, respectively, having the number of carbon atoms designated, appended to one, two, or three aryl groups. The term benzyl as used herein refers to —$CH_2$—$C_6H_5$.

The term "alkyloxy" as used herein refers to an alkyl group linked to an oxygen atom, such as methoxy, ethoxy, and so forth.

The term "halogen" as used herein refer to Cl, Br, F or I substituents.

The term "direct link" as used herein refers to a bond directly linking the substituents on each side of the direct link. When two adjacent substituents are defined as each being a "direct link", it is considered to be a single bond.

Two substituents are "taken together to form a 5–6 membered ring" means that an ethylene or a propylene bridge, respectively, is formed between the two substituents.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methaulonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, and aluminum bases, and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it. The biological properties of the compounds of the present invention can be readily characterized by the methods described in Examples 45 and 46 and by such other methods as are well known in the art.

In addition, the following abbreviations are used in this application:

"ACN" refers to acetonitrile.

"Bn" refers to benzyl.

"Boc" refers to t-butoxycarbonyl.

"BOP" refers to benzotriazol-1-yloxy-tris-(dimethylamino) phosphonium hexafluorophosphate.

"Bu" refers to butyl.

"CBZ" refers to carbobenzoxy.

"DCC" refers to N,N'-dicylcohexylcarbodiimide.

"DCM" refers to dichloromethane.

"DCU" refers to dicyclohexylurea.

"DIC" refers to diisopropylcarbodiimide.

"DIEA" refers to diisopropylethylamine.

"DMAP" refers to 4-dimethylaminopyridine.

"DMF" refers to N,N-dimethylformamide.

"DMSO" refers to dimethylsulfoxide.

"Et" refers to ethyl.

"$Et_2O$" refers to diethyl ether.

"EtOAc" refers to ethyl acetate.

"EtSMe" refers to ethyl methyl sulfide.

"GlyOBn" refers to glycine benzyl ester.

"HF" refers to hydrogen fluoride.

"IBX" refers to o-iodoxybenzoic acid.

"Me" refers to methyl.

"Ph" refers to phenyl.

"Py" refers to pyridyl.

"TFA" refers to trifluoroacetic acid.

"THF" refers to tetrahydrofuran.

"Tos" refers toptoluenesulfonyl.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention. In the processes described above, the final products may, in some cases, contain a small amount of diastereomeric or enantiomeric products; however, these products do not affect their therapeutic or diagnostic application.

In all of the peptides of the invention, one or more amide linkages (—CO—NH—) may optionally be replaced with another linkage which is an isostere such as —CH$_2$NH—, —CH$_2$S—, —CH$_2$—O—, —CH$_2$CH$_2$—, —CH=CH— (cis and trans), —COCH$_2$—, —CH(OH)CH$_2$—, —CH$_2$SO—, and —CH$_2$SO$_2$—. This replacement can be made by methods known in the art. The following references describe preparation of peptide analogs which include these alternative-linking moieties: Spatola, "Peptide Backbone Modifications" (general review) *Vea Data*, Vol. 1, Issue 3, (March 1983); Spatola, "Chemistry and Biochemistry of Amino Acids, Peptides and Proteins," (general review) B. Weinstein, eds., Marcel Dekker, New York, p. 267 (1983); Morley, *Trends Pharm. Sci.* (general review) pp. 463–468 (1980); Hudson, et al., *Int. J. Pept. Prot. Res.* 14:177–185 (1979) (—CH$_2$NH—, —CH$_2$CH$_2$—); Spatola, et al., *Life Sci.* 38:1243–1249 (1986) (—CH$_2$-S); Hann, *J. Chem. Soc. Perkin Trans.* I pp.307–314 (1982) (—CH=CH—, cis and trans); Almquist, et al., *J. Med. Chem.* 23:1392–1398 (1980) (—COCH$_2$—); Jennings-White, et al., *Tetrahedron Lett.* 23:2533 (—COCH$_2$—) (1982); Szelke, et al., European Application EP 45665; CA:97:39405 (1982) (—CH(OH)CH$_2$—); Holladay, et al., *Tetrahedron Lett* 24:4401–4404 (1983) (—CH(OH)CH$_2$—); and Hruby, *Life Sci.* 31:189–199 (1982) (—CH$_2$—S—).

PREFERRED EMBODIMENTS

This invention relates to a new class of cyclic diaza compounds selected from those of general formula I which are potent and specific inhibitors of Xa, their pharmaceutically acceptable compositions thereof, and the methods of using them as therapeutic agents for disease states in mammals characterized by abnormal thrombosis:

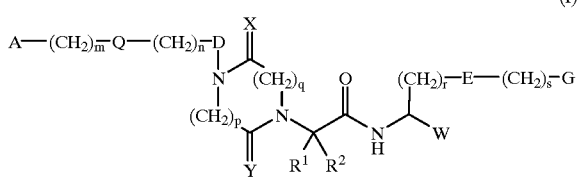

(I)

Wherein:
$R^1$ is selected from the group consisting of H, C$_{1-6}$alkyl, C$_{3-8}$cycloalkyl, C$_{1-3}$alkylaryl. C$_{1-3}$alkyl-C$_{3-8}$cycloalkyl and aryl and $R^2$ is H, or $R^1$ and $R^2$ are taken together to form a carbocyclic ring;
  m is an integer from 0–2;
  n is an integer from 0–6;
  p is an integer from 0–2;
  q is an integer from 1–3;
  r is an integer from 0–4;
  s is an integer from 0–1;
  A is selected from the group consisting of $R^3$, —NR$^3$R$^4$,

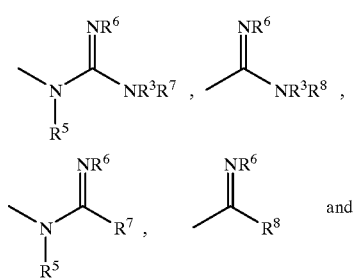

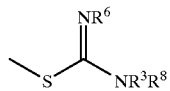

where $R^3$, $R^4$, $R^5$ and $R^6$ are independently selected from the group consisting of H, —OH, C$_{1-6}$alkyl, aryl and C$_{1-4}$alkylaryl; $R^7$ is selected from the group consisting of H, C$_{1-6}$alkyl, aryl and C$_{1-4}$alkylaryl, or can be taken together with $R^5$ or $R^6$ to form a 5–6 membered ring; and $R^8$ is selected from the group consisting of H, C$_{1-6}$alkyl, aryl and C$_{1-4}$alkylaryl, or can be taken together with $R^6$ to form a 5–6 membered ring;

Q is selected from the group consisting of a direct link, C$_{1-6}$alkyl, C$_{3-8}$cycloalkyl. C$_{2-6}$alkenyl, C$_{2-6}$-alkenylaryl, aryl, and a five to ten membered heterocyclic ring system containing 1–4 heteroatoms selected from the group consisting of N, O and S;

D is selected from the group consisting of a direct link, —CO—, —SO$_2$—, —O—CO—, —NR$^9$—SO$_2$— and —NR$^9$—CO—, where $R^9$ is selected from the group consisting of H, —OH, C$_{1-6}$alkyl, aryl and C$_{1-4}$alkylaryl;

E is selected from the group consisting of a direct link, C$_{3-8}$cycloalkyl, aryl, and a five to ten membered heterocyclic ring system containing 1–4 heteroatoms selected from the group consisting of N, O and S;

G is selected from the group consisting of $R^{10}$, —NR$^{10}$R$^{11}$,

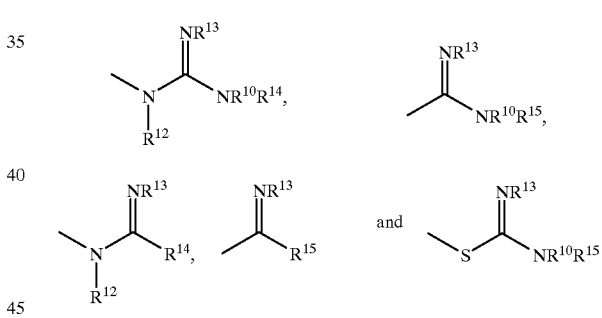

where $R^{10}$, $R^{11}$, $R^{12}$ and $R^{13}$ are independently selected from the group consisting of H, —OH, C$_{1-6}$alkyl, aryl and C$_{1-4}$alkylaryl; $R^{14}$ is selected from the group consisting of H, C$_{1-6}$alkyl, aryl and C$_{1-6}$alkylaryl, or can be taken together with $R^{12}$ or $R^{13}$ to form a 5–6 membered ring; and $R^{15}$ is selected from the group consisting of H, C$_{1-6}$alkyl, aryl and C$_{1-4}$alkylaryl, or can be taken together with $R^{13}$ to form a 5–6 membered ring; with the proviso that when G is $R^{10}$, then E must contain at least one N atom;

X and Y are independently selected from the group consisting of O and H$_2$;

W is selected from the group consisting of H,

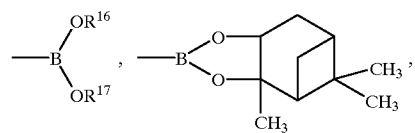

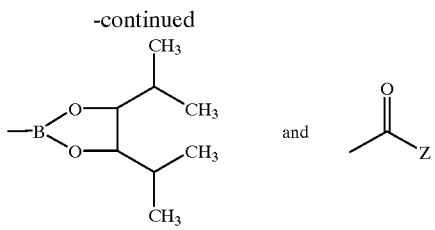 and 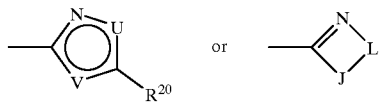

where $R^{16}$ and $R^{17}$ are independently selected from the group consisting of H, $C_{1-3}$alkyl and aryl; and Z is selected from the group consisting of H, —COOR$^{18}$, —CONR$^{18}$R$^{19}$, —CF$_3$, —CF$_2$CF$_3$ and a group having the formula:

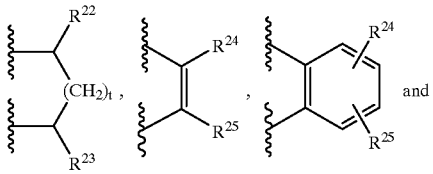

where:

$R^{18}$ and $R^{19}$ are independently selected from the group consisting of H, $C_{1-6}$alkyl, aryl and $C_{1-4}$alkylaryl;

U is selected from the group consisting of —O—, —S—, —N— and —NH—; and

V is selected from the group consisting of —O—, —S—, —N— and —NH—; with the proviso that at least one of U or V is —N— or —NH—;

$R^{20}$ is selected from the group consisting of H, $C_{1-6}$alkyl, $C_{2-6}$alkenyl, $C_{0-6}$alkylaryl, $C_{2-6}$alkenylaryl, $C_{0-6}$alkylheterocyclo, $C_{2-6}$akenylheterocyclo, —CF$_3$ and —CF$_2$CF$_3$;

J is selected from the group consisting of —S—, —SO—, —SO$_2$—, —O— and —NR$^{21}$—, where $R^{21}$ is selected from the group consisting of H, $C_{1-6}$alkyl and benzyl; and L is selected from the group consisting of:

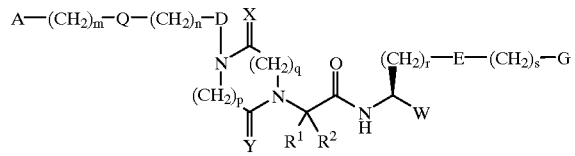

a $C_{6-10}$ heterocyclic ring system substituted by $R^{24}$ and $R^{25}$ and containing 1–4 heteroatoms selected from N, S and O;

where t is an integer from 0–2;

$R^{22}$ and $R^{22}$ are independently selected from the group consisting of H, $C_{1-6}$allyl, aryl, $C_{1-6}$alkylaryl, —COOR$^{26}$, —CONR$^{26}$R$^{27}$, —CN and —CF$_3$;

$R^{24}$ and $R^{25}$ are independently selected from the group consisting of H, $C_{1-6}$alkyl, aryl, $C_{1-6}$alkylaryl, $C_{1-4}$alkyloxy, halogen, —NO$_2$, —NR$^{26}$R$^{27}$, —NR$^{26}$COR$^{27}$, —OR$^{26}$, —OCOR$^{26}$, —COOR$^{26}$, —CONR$^{26}$R$^{27}$, —CN, —CF$_3$, —SO$_2$NR$^{26}$R$^{27}$ and $C_{1-6}$alkyl-OR$^{26}$; and $R^{26}$ and $R^{27}$ are independently selected from the group consisting of H, $C_{1-6}$alkyl, $C_{1-3}$alkylaryl and aryl; and all pharmaceutically acceptable salts and optical isomers thereof.

A preferred embodiment of compounds of general structural formula I have the following stereochemistry:

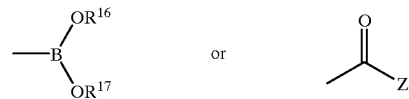

Preferred $R^1$ substituents are H and $C_{1-4}$alkyl; more preferably H and methyl; most preferably H. $R^2$ is preferably H.

The integer "m" is preferably from 0–1; more preferably 0.

The integer "n" is preferably from 0–4.

The integer "p" is preferably from 1–2.

The integer "q" is preferably from 1–2.

The integer "r" is preferably from 0–4.

The integer "s" is preferably 0.

In the various "A" substituents, it is preferred that $R^3$, $R^4$, $R^5$ and $R^6$ are independently selected from the group consisting of H or $C_{1-6}$alkyl; and are more preferably independently selected from the group consisting of H or methyl. It is also preferred that $R^7$ is H, $C_{1-6}$alkyl or taken together with $R^5$ or $R^6$ to form a 5–6 membered ring; and is more preferably H or methyl. It is also preferred that $R^8$ is H, $C_{1-6}$alkyl or taken together with $R^6$ to form a 5–6 membered ring; and is more preferably H or methyl.

Preferred "Q" substitents are a direct link, $C_{1-4}$alkyl, $C_{3-4}$cycloalkyl, aryl, or a five to ten membered heterocyclic ring system. More preferably, Q is $C_{1-4}$alkyl, aryl, or a five to ten membered heterocyclic ring system.

D is preferably a direct link, —CO— or —SO$_2$.

E is preferably a direct link

In the "G" substituent, it is preferred that $R^{10}$, $R^{11}$, $R^{12}$ and $R^{13}$ are independently selected from the group consisting of H and $C_{1-6}$alkyl, more preferably H and methyl.

X is preferably H$_2$.

Y is preferably O.

W is preferably:

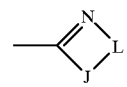

where $R^{16}$ is preferably H and $R^{17}$ is preferably H.

Z is preferably H, —COOR$^{18}$, —CONR$^{18}$R$^{19}$ or a group having the formula:

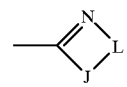

For —COOR$^{18}$, $R^{18}$ is preferably H, $C_{1-6}$alkyl or $C_{1-4}$alkylaryl. For —CONR$^{18}$R$^{19}$, $R^{18}$ is preferably H and $R^{19}$ is preferably $C_{1-4}$alkylaryl.

J is preferably —S—, —O— or —NR$^{21}$—, where $R^{21}$ is preferably H or methyl, more preferably H.

L is preferably selected from the group consisting of:

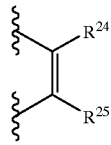 and 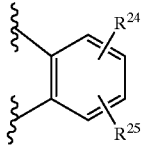

L is more preferably

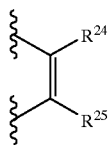

$R^{24}$ and $R^{25}$ are preferably independently selected from the group consisting of H, —O— $R^{26}$, —COOR$^{26}$, —CONR$^{26}$R$^{27}$ or —CF$_3$; more preferably H.

When L is:

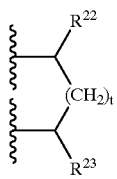

then $R^{22}$ is preferably H and $R^{23}$ is preferably H.

When Z is:

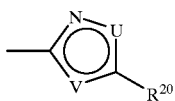

then $R^{20}$ is preferably —CF$_3$ or —CF$_2$CF$_3$.

In one preferred embodiment of the invention, m and s are O, Y is O, $R^1$ and $R^2$ are H and W is —C(O)—Z. This is also illustrated as a preferred group of compounds defined by the general structural formula II as:

(II)

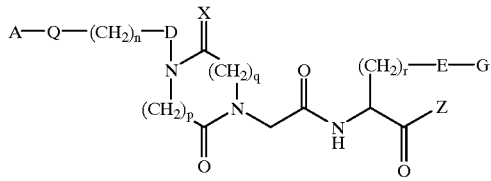

A preferred embodiment of compounds of general structural formula II have the following stereochemistry:

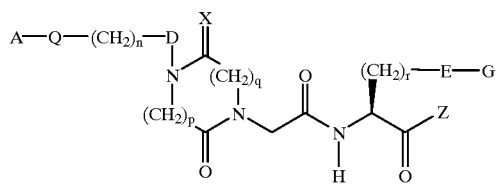

In another preferred embodiment of the invention, m and s are O, Y is O, X is H$_2$, $R^1$ and $R^2$ are H and W is —C(O)—Z. This is also illustrated as a preferred group of compounds defined by the general structural formula III as:

(III)

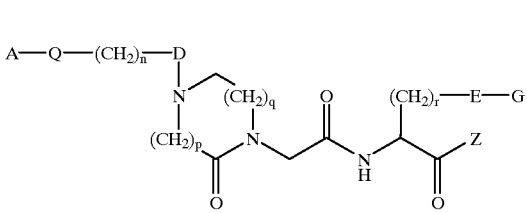

A preferred embodiment of compounds of general structural formula III have the following stereochemistry:

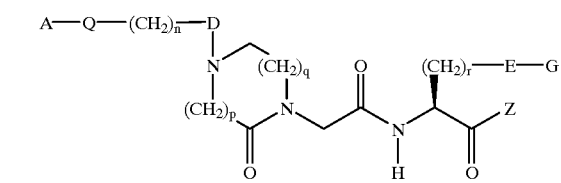

In another preferred embodiment of the invention, m and s are O, r is 3, D is —SO$_2$, Y is O, X is H$_2$, $R^1$ and $R^2$are H, E is a bond, G is:

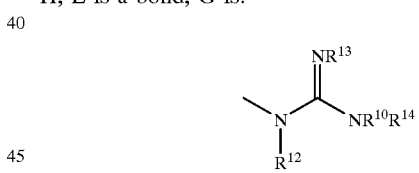

where $R^{10}$, $R^{12}$, $R^{13}$ and $R^{14}$ are all H, and W is —C(O)—Z. This is also illustrated as a preferred group of compounds defined by the general structural formula IV as:

(IV)

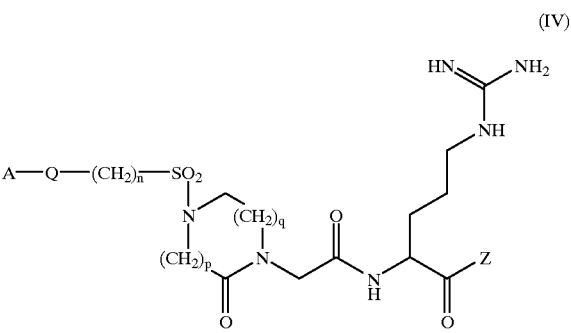

A preferred embodiment of compounds of general structural formula IV have the following stereochemistry:

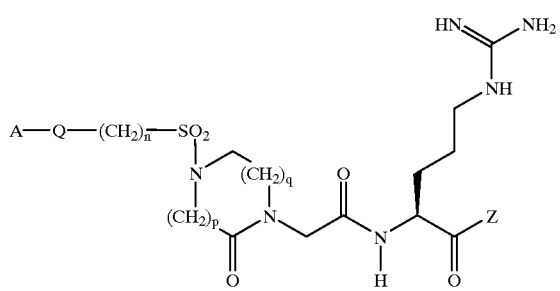

This invention also encompasses all pharmaceutically acceptable isomers, salts, hydrates and solvates of the compounds of formulas I, II, III and IV. In addition, the compounds of formulas I, II, III and IV can exist in various isomeric and tautomeric forms, and all such forms are meant to be included in the invention, along with pharmaceutically acceptable salts, hydrates and solvates of such isomers and tautomers.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

The following structures are illustrative of the compounds of the present invention and are not intended to be limiting in any manner. It is to be noted that in the compounds of the invention, certain substituents are present between two other substituents. For example, Q is positioned between A—$(CH_2)_m$— and —$(CH_2)_n$—D—. Accordingly, substituents such as Q are illustrated below as having two "dangling" bonds, the bond on the left representing a direct link to substituent A—$(CH_2)_m$— and the bond on the right representing a direct link to —$(CH_2)_n$—D—. Therefore, the general formula of A—$(CH_2)_m$—Q—$(CH_2)_n$—D— where Q is phenyl can be written as:

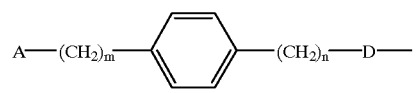

Q, a phenyl group, would then be written as follows in the tables below:

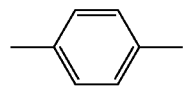

Other substituents in the table below may also be presented as having one or two similar "dangling" bonds. It is understood that these represent direct links to the adjacent substituent(s). It is also understood that the compounds illustrated below can exist as other isomers, and the isomeric form illustrated herein is not intended to be limiting in any manner.

The invention encompasses compounds of general structural formula V, where X and Y are both O; D is a direct link; m and s are 0; p and q are 1; and $R^1$ and $R^2$ are H:

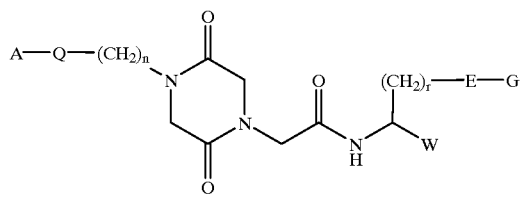

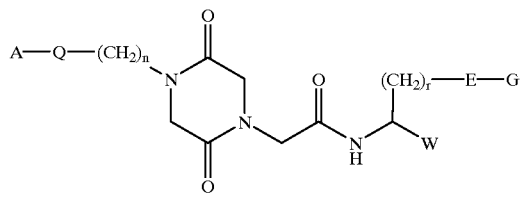

| # | A | Q | n | r | E | G | W |
|---|---|---|---|---|---|---|---|
| 10 | H | -N(methylpiperidine)- | 2 | 3 | direct link | -NH-C(=NH)-NH₂ | -C(=O)-C(=O)-NH-CH₂-CH₂-Ph |
| 11 | H₂N-C(=NH)- | -N(methylpiperidine)- | 2 | 3 | direct link | -NH-C(=NH)-NH₂ | -C(=O)-C(=O)-NH-CH₂-CH₂-Ph |

The invention also encompasses compounds of general structural formula VI, where X is H₂ and Y is O; D is SO₂; m, n and s are 0; p and q are 1; A is H; and $R^1$ and $R^2$ are H:

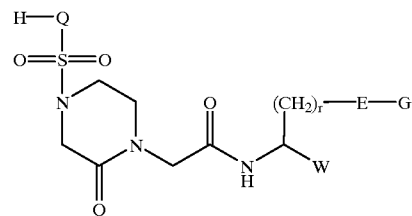

| # | Q | r | E | G | W |
|---|---|---|---|---|---|
| 1 | 2,6-dimethylnaphthalene | 3 | direct link | -NH-C(=NH)-NH₂ | 2-acetylthiazole |
| 2 | 4-methylstyrene | 1 | 2,5-pyridyl | -NH₂ | 2-acetylbenzoxazole |
| 3 | 3-chloro-2,7-dimethylnaphthalene | 3 | direct link | -NH-C(=NH)-NH₂ | 2-acetylthiazole |

-continued (VI)

| # | Q | r | E | G | W |
|---|---|---|---|---|---|
| 4 | 3,5-dimethylisoquinoline | 2 | 4,6-dimethylpyrimidine | H | 2-acetylthiazole |
| 5 | 2,5-dimethylthiazole | 0 | 1-methyl-4-piperidinyl | CH₃-C(=N-OH)-NH₂ | 1-methyl-2-acetylimidazole |
| 6 | N-(2,4-dimethylphenyl)acetamide | 4 | direct link | —NH₂ | 2-acetylthiazole |
| 7 | 4-methyl-propenylbenzene | 3 | direct link | —NH-C(=NH)-NH₂ | 2-acetylthiazole |
| 8 | 4-methyl-ethylbenzene | 3 | direct link | —NH-C(=NH)-NH₂ | 2-acetylthiazole |
| 9 | 5-chloro-3-methylbenzothiophene-2-sulfonyl | 3 | direct link | —NH-C(=NH)-NH₂ | 2-acetylisothiazole |
| 10 | 5-chloro-1-naphthalenesulfonyl | 3 | direct link | —NH-C(=NH)-NH₂ | 2-acetylisothiazole |
| 11 | 5-(2-pyridyl)thiophene-2-sulfonyl | 3 | direct link | —NH-C(=NH)-NH₂ | 2-acetylisothiazole |

-continued (VI)

| # | Q | r | E | G | W |
|---|---|---|---|---|---|
| 12 | 8-quinolinyl-(SO$_2$)— | 3 | direct link | —NH-C(=NH)-NH$_2$ | acetyl-isothiazole |
| 13 | benzofurazan-4-yl-(SO$_2$)— | 3 | direct link | —NH-C(=NH)-NH$_2$ | acetyl-isothiazole |
| 14 | (Br)Cl-phenyl-(SO$_2$)— | 3 | direct link | —NH-C(=NH)-NH$_2$ | acetyl-isothiazole |
| 15 | 3,5-dimethylisoxazol-4-yl-(SO$_2$)— | 3 | direct link | —NH-C(=NH)-NH$_2$ | acetyl-isothiazole |
| 16 | H$_3$CO-phenyl-(SO$_2$)— | 3 | direct link | —NH-C(=NH)-NH$_2$ | acetyl-isothiazole |

The invention also encompasses compounds of general structural formula VII, where X is H$_2$ and Y is O; D is SO$_2$; m and s are 0; r is 3; q is 1; E is a direct bond; and R$^1$ and R$^2$ are H;

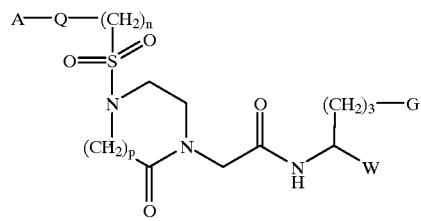

(VII)

| # | A | Q | n | p | G | W |
|---|---|---|---|---|---|---|
| 1 | phenyl | p-phenylene | 0 | 1 | N-hydroxyguanidine | oxazoline-2-carbonyl |
| 2 | H | 6-chloro-2,7-naphthylene | 0 | 2 | guanidine | benzothiazole-2-carbonyl |
| 3 | —CH₃ | 1,4-piperidinylene | 2 | 1 | guanidine | thiazole-2-carbonyl |
| 4 | H | 2,6-naphthylene | 0 | 2 | guanidine | thiazole-2-carbonyl |
| 5 | H | p-phenylene | 1 | 2 | guanidine | thiazole-2-carbonyl |
| 6 | —NH₂ | p-phenylene | 0 | 2 | guanidine | thiazole-2-carbonyl |

The invention also encompasses compounds of general structural formula VIII, where X is H$_2$ and Y is O; D is SO$_2$; m and s are 0; and E is a direct bond:

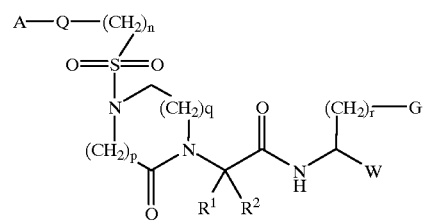

(VIII)

| # | A | Q | n | p | q | R¹ | R² | r | G | W |
|---|---|---|---|---|---|---|---|---|---|---|
| 1 | acetamidine (HN=C(NH2)-) | 1,4-phenylene | 1 | 1 | 1 | —CH₃ | H | 3 | N,N-dimethylguanidinyl | 3-acetyl-5-(trifluoromethyl)-1,2,4-oxadiazole |
| 2 | H | 3-chloro-2,6-naphthylene | 0 | 1 | 2 | H | H | 3 | N-methylguanidinyl | 2-acetylbenzothiazole |
| 3 | acetimidoyl (HN=C(CH3)-) | 1,4-phenylene | 1 | 1 | 1 | H | H | 4 | —N(CH₃)₂ | trifluoroacetyl |
| 4 | H | 1,4-cyclohexylene | 2 | 2 | 1 | H | H | 4 | N-methylacetamidinyl | 2-acetyl-1-methylimidazole |
| 5 | HN=C(NH2)- | 1,4-phenylene | 1 | 1 | 1 | H | H | 3 | N-benzylacetamidinyl | 2-acetylthiazole |
| 6 | H | 3-chloro-2,6-naphthylene | 1 | 2 | 1 | —CH₃ | H | 3 | N-methyl-N'-phenylguanidinyl | 2-acetylthiazole |
| 7 | HN=C(NH2)- | 1,4-phenylene | 1 | 1 | 1 | cyclopropyl | | 3 | N,N-dimethylguanidinyl | 3-acetyl-5-(trifluoromethyl)-1,2,4-oxadiazole |

The invention also encompasses compounds of general structural formula IX, where X is $H_2$ and Y is O; D is $SO_2$; m is 0; P is 1: and $R^1$ and $R^2$ are H:

(IX)

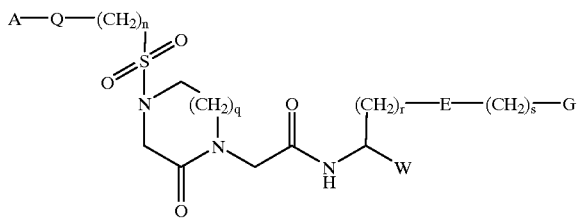

| # | A | Q | n | q | r | E | s | G | W |
|---|---|---|---|---|---|---|---|---|---|
| 1 | H₃C— | 2-methyl-5-methyl-tetrahydroisoquinoline | 0 | 1 | 1 | 1,4-cyclohexyl | 1 | —NH₂ | 2-acetylthiazole |
| 2 | (CH₃)₂C=NH | 1,4-dimethylpiperazine | 2 | 2 | 1 | 2,5-pyridyl | 0 | amidoxime (N—OH, NH₂) | —C(O)COOH |

The invention also encompasses compounds of general structural formula X, where $R^2$ is H; X is $H_2$ and Y is O; D is —O—OC—; E is a direct ink; r is 3; m and s are 0:

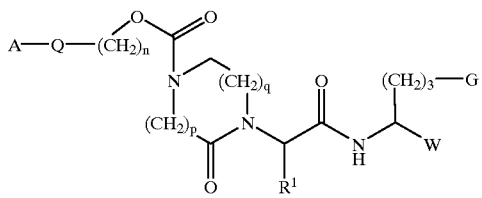

(X)

| # | A | Q | n | p | q | R¹ | G | W |
|---|---|---|---|---|---|---|---|---|
| 1 | H | —CH₂—C(CH₃)₂— | 0 | 2 | 1 | H | N-methyl-N-methylguanidine | 2-acetylthiazole |
| 2 | H | 1,4-phenylene (p-xylyl) | 1 | 1 | 1 | H | guanidine (—NH—C(=NH)NH₂) | 2-acetylthiazole |

The invention also encompasses compounds of general structural formula Xl, where X is $H_2$ and Y is O; D is CO; p and q are 1; m and s are 0; and $R^1$ and $R^2$ are H:

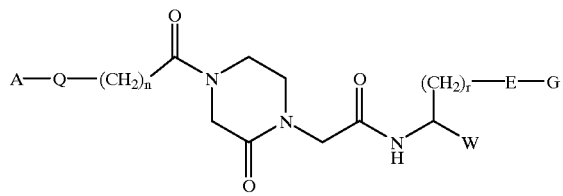

| # | A | Q | n | r | E | G | W |
|---|---|---|---|---|---|---|---|
| 1 | H | 2-methyl-benzimidazole | 2 | 3 | direct link | N-hydroxyguanidine (methyl) | 2-acetyl-4,5-dihydrooxazole |
| 2 | H₂N— | 2-methylbenzothiazole | 1 | 3 | 2,4-imidazole | —NH₂ | COCF₂CF₃ |
| 3 | HO— | p-phenylene | 2 | 1 | 2-methylbenzimidazole | N-methylacetamidine | 2-acetylbenzoxazole |

The invention also encompasses compounds of general structural formula XII, where X is $H_2$ and Y is O; D is CO; p and q are 1; m and n are 1; and $R^1$ and $R^2$ are H:

The invention also encompasses compounds of general structural formula XIII, where $R^2$ is $H_2$ and Y is O; D and E are direct links; r is 3; and m and s are 0:

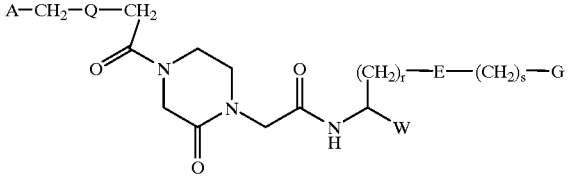

| # | A | Q | r | E | s | G | W |
|---|---|---|---|---|---|---|---|
| 1 | H₂N— | p-phenylene | 2 | 4-methylpyridine | 0 | H | COCF₃ |
| 2 | H₂N-C(=NH)-NH-methyl | p-phenylene | 1 | p-phenylene | 1 | N-methylguanidine | 2-acetylthiazole |

(XIII)

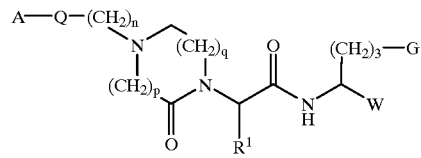

| # | A | Q | n | p | q | R¹ | G | W |
|---|---|---|---|---|---|---|---|---|
| 1 | acetamidine | 4-methylpiperidinyl | 1 | 1 | 1 | —CH₃ | N,N-dimethylguanidine | 5-(trifluoromethyl)-1,2,4-oxadiazol-3-yl ketone |
| 2 | H | 4-methylpiperidinyl | 2 | 0 | 2 | H | N-methylguanidine | thiazol-2-yl ketone |
| 3 | acetamidine | 1,4-phenylene | 0 | 0 | 1 | H | N-methylguanidine | thiazol-2-yl ketone |
| 4 | acetamidine | 1,3-phenylene | 1 | 0 | 3 | H | N-methylguanidine | thiazol-2-yl ketone |

The invention also encompasses compounds of general structural formula XIV, where R² is H; X is H₂; Y is O; D is —NR⁹—SO₂; m and s are 0; p and q are 1; and G is —NH₂:

(XIV)

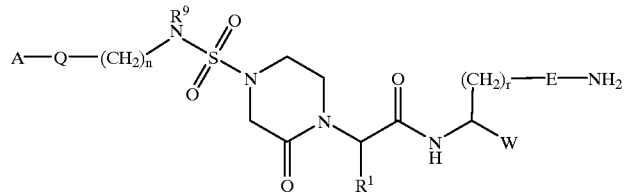

| # | A | Q | n | r | R⁹ | E | R¹ | W |
|---|---|---|---|---|---|---|---|---|
| 1 | H | 1,4-phenylene | 2 | 1 | H | 1,4-cyclohexylene | H | thiazol-2-yl ketone |

(XIV)

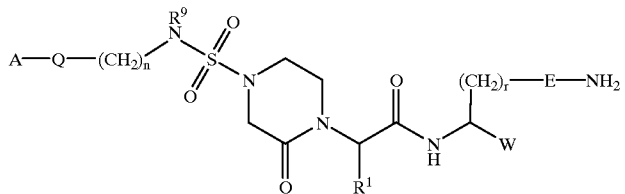

| # | A | Q | n | r | R⁹ | E | R¹ | W |
|---|---|---|---|---|---|---|---|---|
| 2 | H₂N— | (2,4-pyridyl) | 2 | 1 | H | (2,5-pyridyl) | H | -CH(CH₃)-COOH |

The invention also encompasses compounds of general structural formula XV, where X is $H_2$ and Y is O; D is $-NR^9-CO$: A is $-C(NH_2)H$; m and s are 0: p and q are 1: E is a direct link; $R^1$ is $-CH_3$; and $R^2$ is H:

The invention also encompasses compounds of general structural formula XVI, where X and Y are $H_2$; D is a direct link; m and s are O; q and p are 1; and $R^1$ and $R^2$ are H:

(XV)

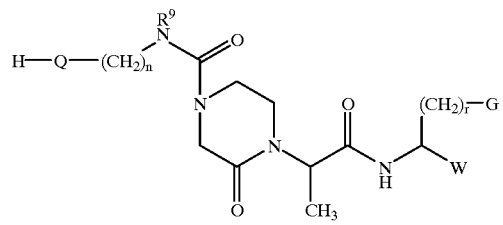

| # | Q | n | R⁹ | G | r | W |
|---|---|---|---|---|---|---|
| 1 | (2,6-naphthyl) | 1 | H | -NH-C(=NH)-NH₂ | 3 | C(=O)-thiazol-2-yl |
| 2 | (1-methylpiperidin-4-yl) | 2 | —CH₃ | —NH₂ | 4 | C(=O)-thiazol-2-yl |

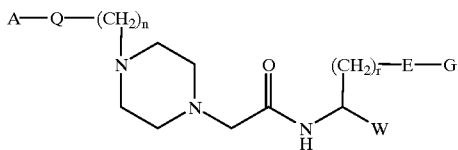

As mentioned above, the compounds of this invention find utility as therapeutic agents for disease states in mammals which have disorders of coagulation such as in the treatment or prevention of unstable angina, refactory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine. glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, microencapsulation, oral dosage formulations and topical formulations such as ointments, drops and dermal patches. The compounds of this invention are desirably incorporated into shape articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidyicholines The compounds of this invention may also be delivered by the use of antibodies. antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartaride-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterle access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

PREPARATION OF THE DISCLOSED COMPOUNDS

The compounds of the present invention may be synthesized by either solid or liquid phase methods described and referenced in standard textbooks, or by a combination of both methods. These methods are well known in the art. See. Bodanszky. "The Principles of Peptide Synthesis". Hafner. et al.. Eds.. Springer-Verlag. Berlin. 1984.

Starting materials used in any of these methods are commercially available from chemical vendors such as Aldrich Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated. The reaction products are isolated and purified by conventional methods, typically by solvent extraction into a compatible solvent. The products may be further purified by column chromatography or other appropriate methods. Most compounds are purified by reversed-phase HPLC and characterized by ion-spray mass spectrometry.

During the synthesis of these compounds, the functional groups of the amino acid derivatives used in these methods are protected by blocking groups to prevent side reactions during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

The compounds of this invention may be preferably prepared by a) coupling the carboxylic acid of formula (a) to the amine of formula (b)

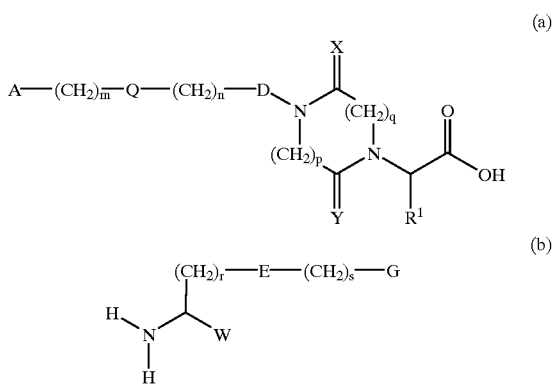

by the standard amide bond formation strategies, or b) where X is $H_2$, D is —$SO_2$— or —CO—, reacting the cyclic amine of formula (c) with the sulfonyl halide of formula (d) or with the carboxylic acid of formula of (e) through standard amide bond or sulfonamide formation strategies,

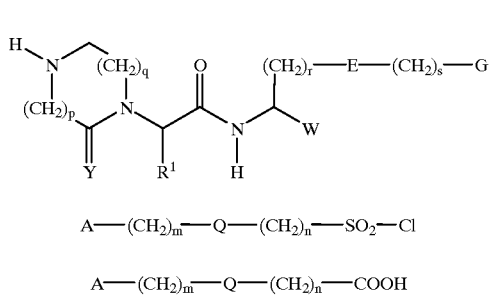

The compounds of formula (b) wherein W is H can be prepared by the methods disclosed in WO 96/01338; WO 96/24609; Feng, et al., WO 96/31504; and WO 96/32110, the disclosures of which are incorporated herein by reference.

The compounds of formula (b) wherein W is a boron containing compound can be prepared by the methods disclosed in J. Org. Chem. 60:3717–3722 (1995) and de Nanteuil, et al., EP 688,788, the disclosures of which are incorporated herein by reference.

The compounds of formula (b) wherein W is —C(O)—Z, where Z is H, may be prepared by the methods disclosed in WO 93/15756, supra, Vlasuk, et al., WO 94/17817; Abelman, et al., WO 94/21673; Webb, et al., WO 94/08941; Veber, et al., WO 94/25051; Levy, et al., WO 95/35312; Semple, et al., WO 95/35313; Abelman, et al., WO 95/28420: and Abelman, et al., WO 96/19493, the disclosures of which are incorporated herein by reference.

The compounds of formula (b) wherein W is —C(O)—Z, where Z is —$COOR^{18}$ or —$CONR^{18}R^{19}$, may be prepared by the methods disclosed in WO 94/2505 1, supra, WO 94/08941, supra, and WO 94/21673, supra, the disclosures of which are incorporated herein by reference.

The compounds of formula (b) wherein W is —C(O)—Z, where Z is —$CF_3$ or —$CF_2CF_3$, may be prepared by the methods disclosed in Schacht, et al., GB 2287027, the disclosure of which is incorporated herein by reference.

The compounds of formula (b) wherein W is —C(O)—Z, where Z is:

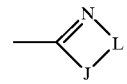

and J is —O—, —SO— or —$SO_2$— can be readily synthesized by the methods disclosed in Costanzo, et al., U.S. Pat. No. 5,523,308; Di Maio, et al., WO 96/19483; U.S. Pat. No. 5,164,371; J. Am. Chem. Soc. 114: 1854–1863 (1992); J. Med. Chem. 38:76–85 (1995); and J. Med. Chem. 37:3492–3502 (1994). Lastly, fragments where J is —$NR^{21}$—, where $R^{21}$ is H, $C_{1-6}$alkyl or benzyl, can be synthesized by techniques illustrated in J. Med. Chem. 37:3492–3502 (1994). All of these references are incorporated herein by reference.

The compounds of formula (b) wherein W is —C(O)—Z, where Z is:

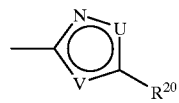

and U and V are the various substituents (—O—, —S—, —N—, —NH—) may be prepared by the methods disclosed in J. Med. Chem. 38: 1355–1371 (1995) and J. Med. Chem. 37: 2421–2436 (1994), the disclosures of which are incorporated herein by reference.

The starting compounds of formula (a), (c), (d) and (e) are either known compounds or can be produced by known methods (Heitsch, et al., Canadian Patent No. 2,071,744; Sugihara, et al., Canadian Patent No. 2,126,026; Baker, et al., EP 365,992; U.S. Pat. No. 4,251,438; Carr, et al., U.S. Pat No. 4,341,698; Goldman, et al., U.S. Pat No. 5,120,718; Biswanath, et al., U.S. Pat No. 5,164,388; Duggan, et al., U.S. Pat. No. 5,281,585; Sugihara, et al., U.S. Pat No. 5,294,713; Bovy, et al., WO 95/06038; WO 95/35308; J. Chem Soc. Perkin Trans. I 1687–1689 (1989); and Int. J. Peptide Protein Res. 37:468–475 (1991)) or prepared by the methods shown in the following reaction formulae, where P and R are protecting groups:

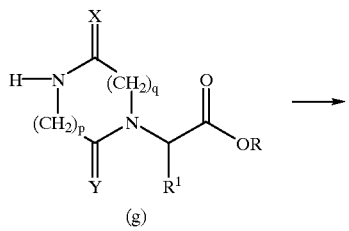

-continued
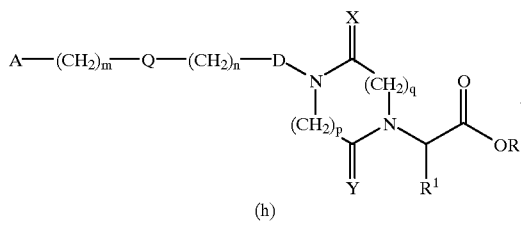
(h)
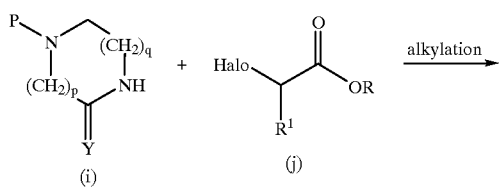
(a)
and:
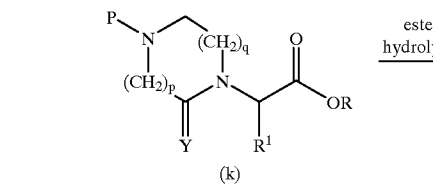
(i) (j)
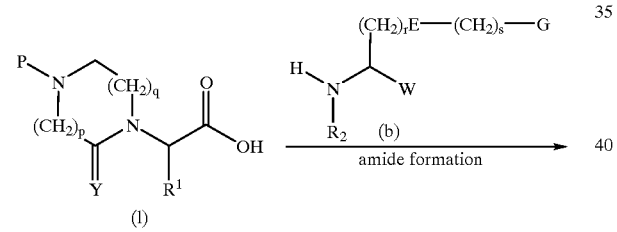
(l)
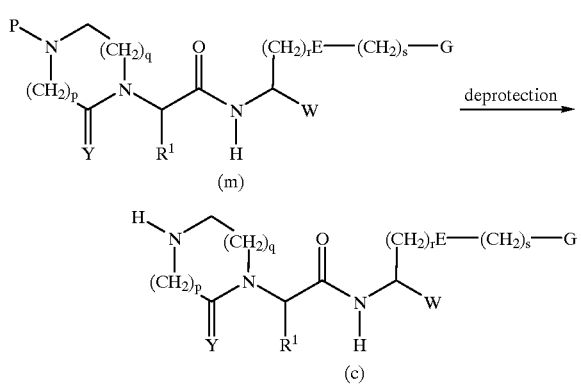
(m)
(c)
The following reaction schemes are more specific illustrations of the above reaction formulae. The chemical reactions described in each scheme can easily be modified and combined with other techniques that are well known in the art to produce other compounds within the scope of the invention.
Scheme I
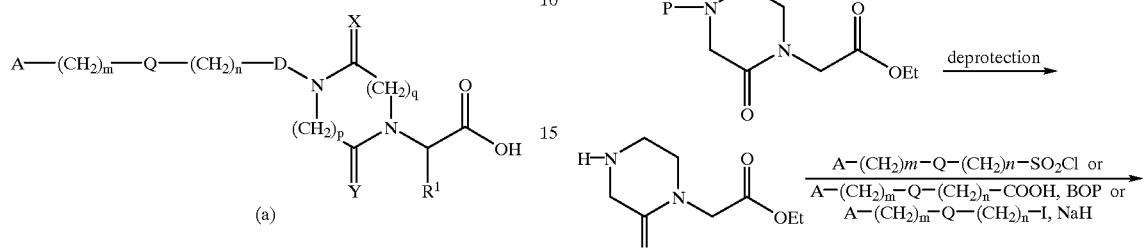
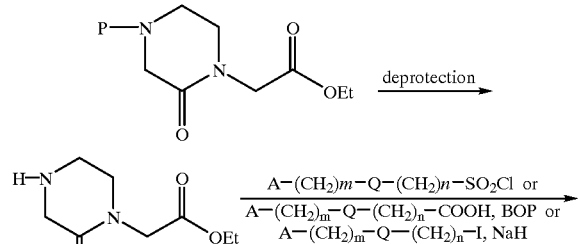
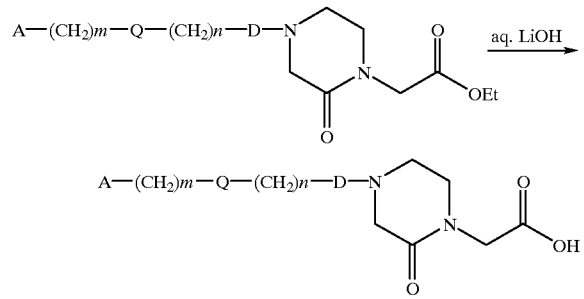
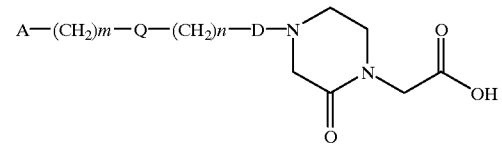
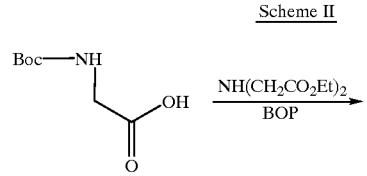
Scheme II
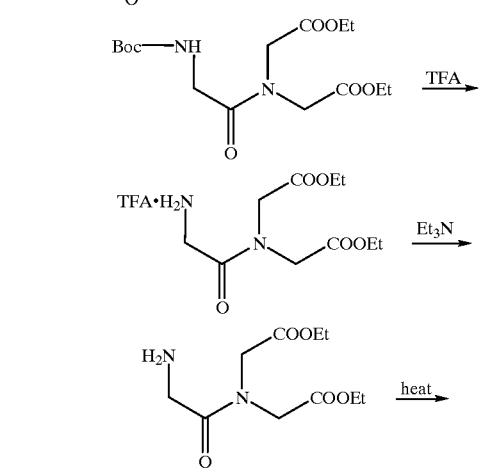
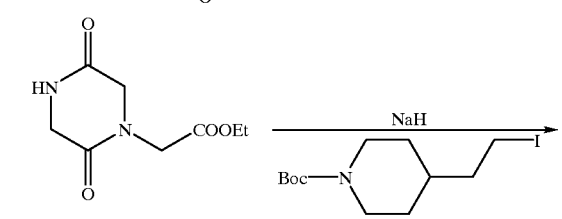

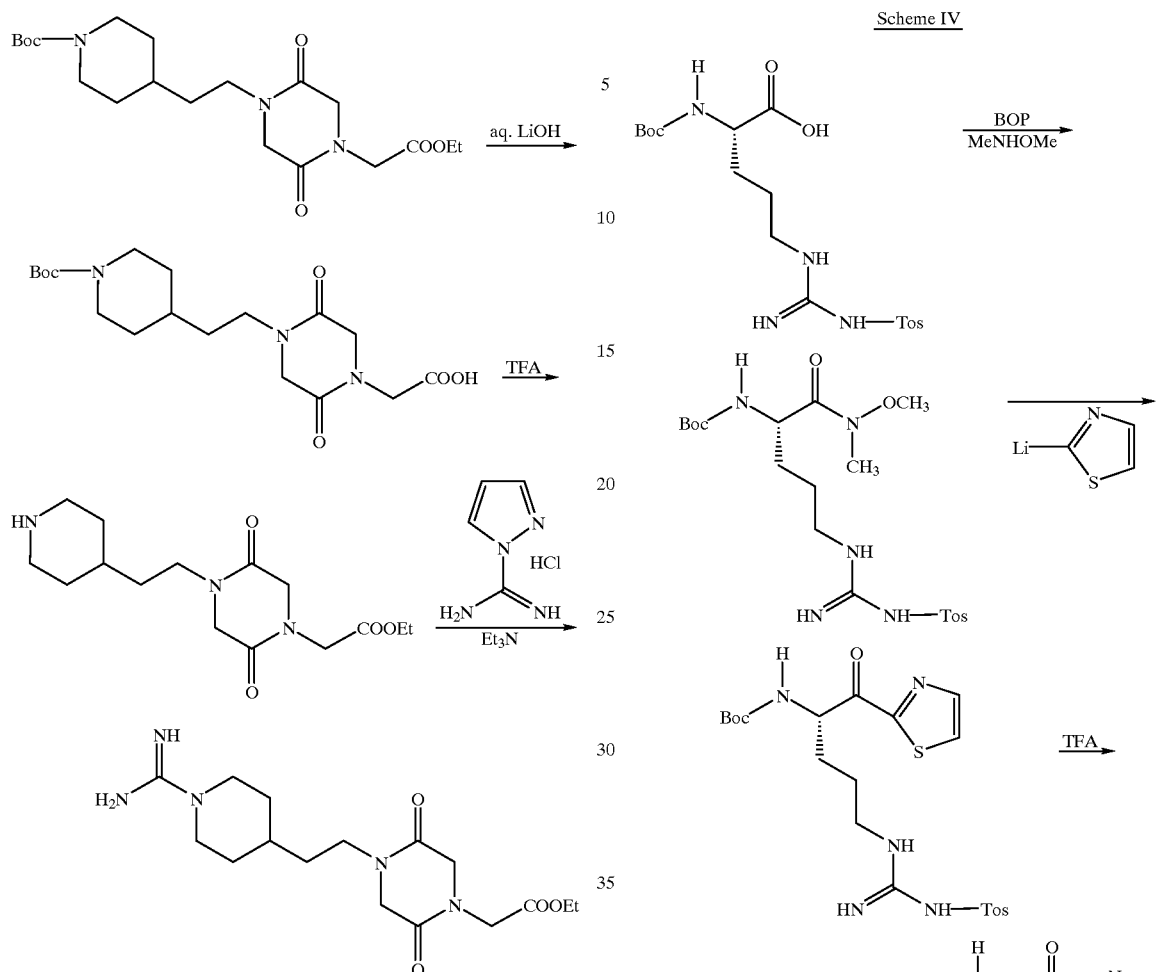
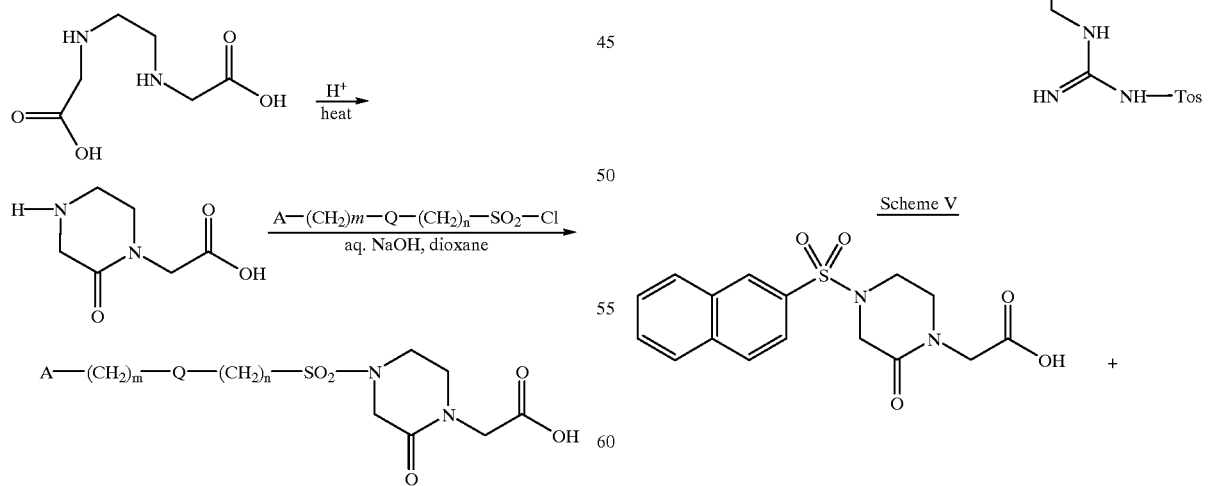

47
-continued
48
Scheme VII
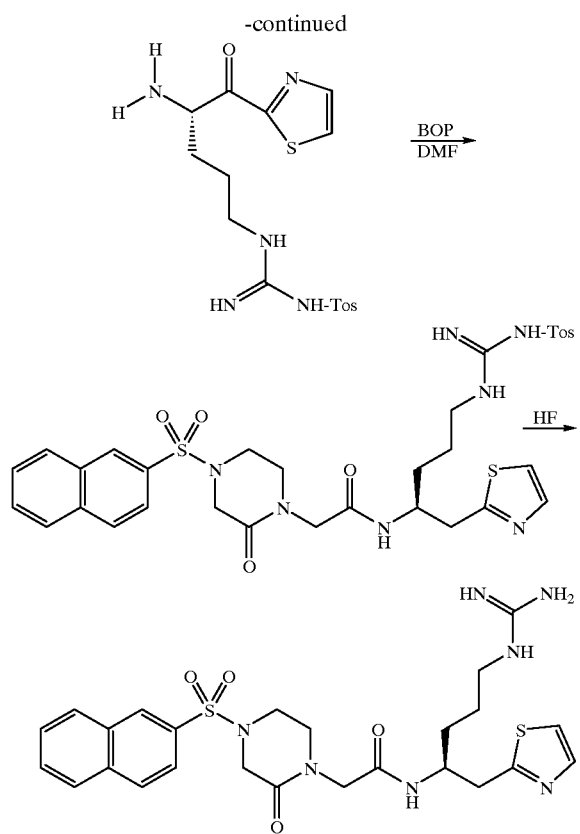
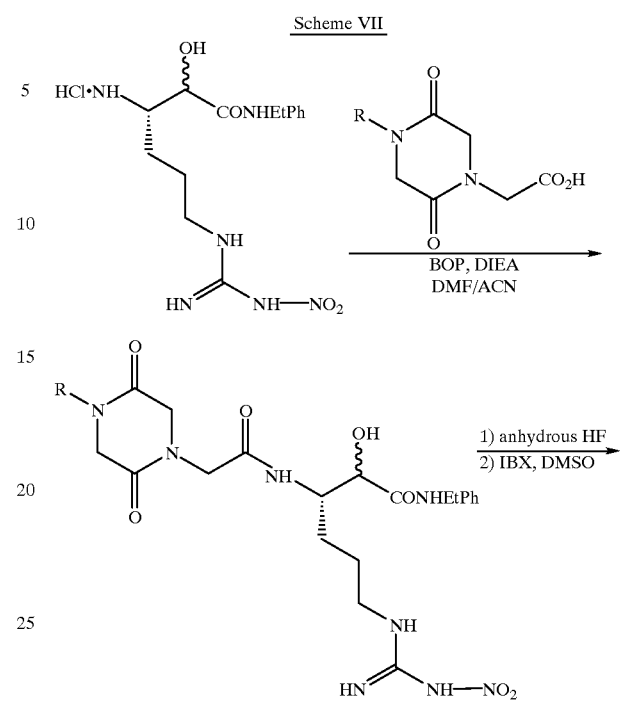
Scheme VI
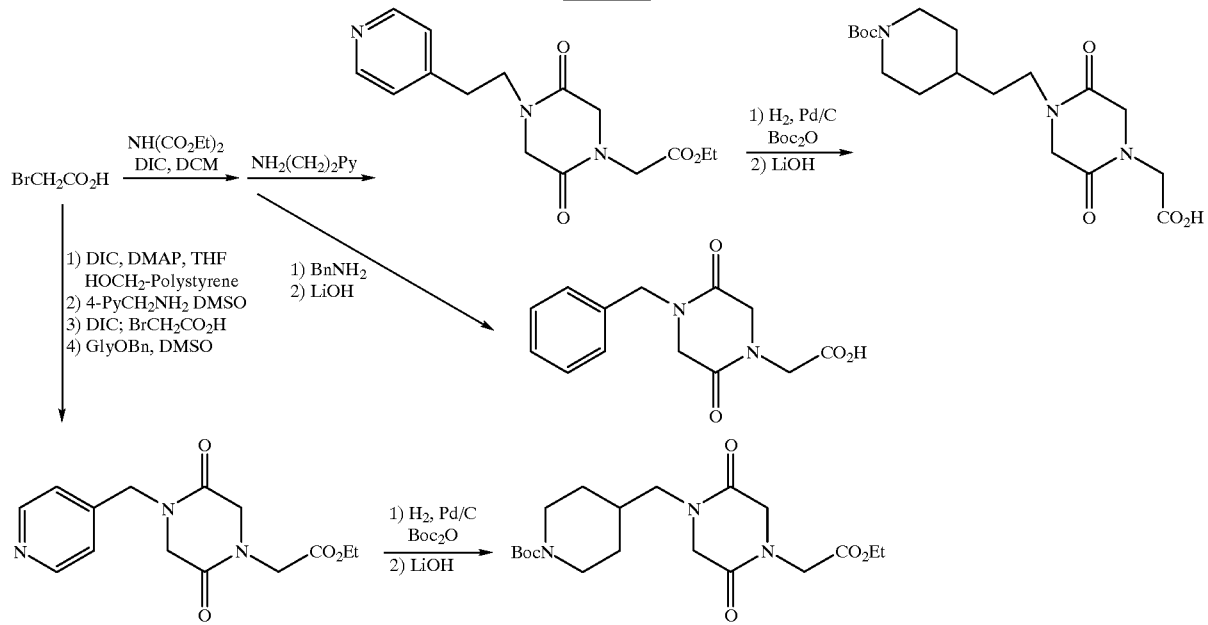

-continued

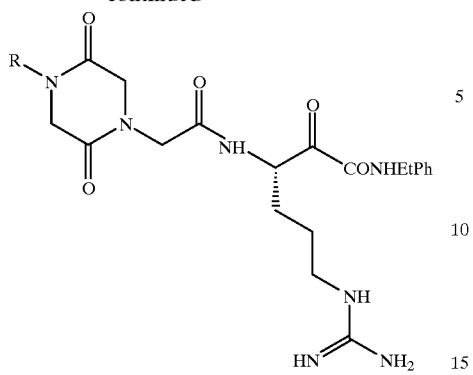

where IBX is: 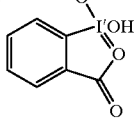

Without further elaboration, it is believed that one skilled in the art can utilize the present invention to its fullest extent Therefore, the following preferred specific embodiments are to be construed as merely illustrative and do not limit the remainder of the disclosure in any way whatsoever.

EXAMPLE 1

Preparation of:

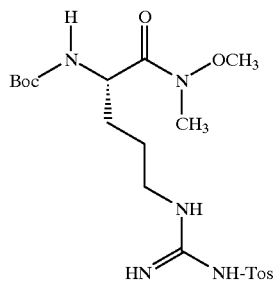

To a suspension of Boc-Arg(Tos)OH (2 g, 4.7 mmol) in DMF (20 mL) at 0° C. was added MeNHOMe•HCl (1 g, 10.3 mmol), DIEA (6 mL) and BOP (2.5 g, 5.6 mmol). The solution was stirred at 0° C. for 10 hours. DMF was evaporated by vacuum. The oily residue was dissolved in EtOAc (200 mL) and water (20 mL). The organic layer was washed with sat. NaHCO$_3$, water (20 mL), 1 M HCl (10 mL) and sate NaCl (2×20 mL). The organic layer was dried over MgSO$_4$, filtered and evaporated to give a suspension. The suspension was filtered, and the solid was washed with cold EtOAc (10 mL) and dried to give Boc-Arg(Tos)-N(Me)OMe, shown above, (1.5 g. 70% yield).

FAB-MS (M+H)+=472.

EXAMPLE 2

Preparation of:

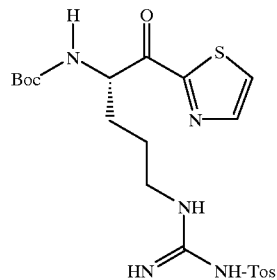

To a solution of thiazole (2.5 g, 29 mmol) in THF (25 mL) at −78° C. was added n-Budi (1.6 M in hexane, 19 mL) dropwise. The mixture was stirred for 30 minutes. Then a solution of Boc-Arg(Tos)N(Me)OMe, from Example 1, (1.7 g, 3.6 mmol) in THF (50 mL) was added to the lithiothiazole mixture at −78° C. The solution was stirred for 2 hours. 1 M HCl (30 mL) was added to the reaction mixture and warmed to room temperature. The mixture was extracted with EtOAc (100 mL). The organic layer was washed with sat NaCl (30 mL), dried over MgSO$_4$, filtered and evaporated. The crude oily residue was purified by flash column chromatography over SiO$_2$ (50% EtOAc in CH$_2$Cl$_2$) to give Boc-Arg(Tos)-thiazole, shown above, (1.5 g, 84% yield) as a powder.

DCI-MS (M+H)+=496

EXAMPLE 3

Preparation of:

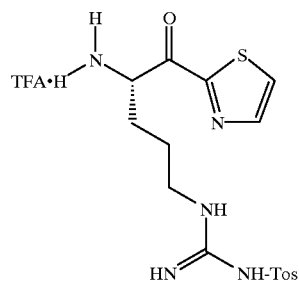

To a solution of Boc-Arg(Tos)-thiazole from Example 2, (300 mg, 0.6 mmol) in CH$_2$Cl$_2$ (10 mL) at 0° C., was added TFA (10 mL). The solution was stirred at 0° C. for 2 hours. The solvent and excess TFA were evaporated to give an oily residue which was used directly without further purification.

EXAMPLE 4

Preparation of Ethyl 2-(4-benzyloxycarbonyl-2-oxopiperazino)acetate:

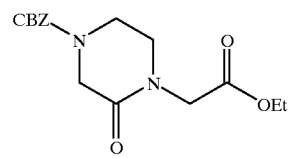

To a solution of 4-benyloxycarbonylpiperazin-2-one (M.W.=234.26, 2.34 g, 10 mmol) in anhydrous THF (150 mL) at −78° C. under argon was added lithium bis (trimethylsilyl) amide (1 M in THF, 12 mL, 12 mmol) dropwise. The mixture was stirred at −78° C. for 30 min Ethyl iodoacetate (M.W.−214, 2.14 g, 10 mmol) was added to the mixture at −78° C., stirred, warmed up to −10° C., and then kept in the freezer over night. The reaction was quenched by adding 1N HCl (60 mL) and extracted with EtOAc (200 mL+100 mL). The combined organic layers were washed with sat. NaCl three times, dried with MgSO$_4$, and evaporated to give the crude title compound as a yellowish oil. Reversed-phase HPLC purification afforded the pure compound in 81% yield.

TLC: Rf=0.45 (EtOAc/MeOH=20:1)
MS:(M+H)+=321.0

EXAMPLE 5

Preparation of Ethyl 2-(2-oxopiperazino) acetate:

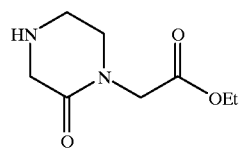

To a solution of the compound of Example 4 (M.W.=320, 1.7 g, 5.3 mmol) in MeOH (50 mL) was added 150 mg of wet 5% palladium on carbon. The suspension was treated with hydrogen at atmospheric pressure overnight, then filtered with the help of Celite. The solvent was removed to give 1.0 g (yield 100%) of the title compound as a yellowish oil.

TLC: Rf=0.34 (CH$_2$Cl$_2$/MeOH=10:1)
MS: (M+H)+=187.3

EXAMPLE 6

Preparation of Ethyl 2-[4-(2-naphthylsulfonyl)-2-oxopiperazino] acetate:

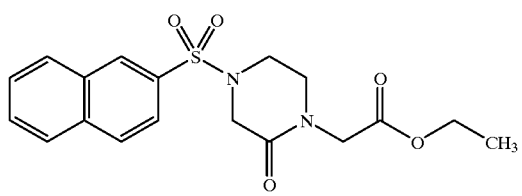

To a solution of the compound of Example 5 (M.W.=186, 100 mg, 0.54 mmol) in CH$_2$Cl$_2$ (10 mL ) at 0° C. under argon, was added 0.20 mL (1.15 mmol) of DIEA 2-Naphthalenesulfonyl chloride (M.W.=227, 146 mg, 0.64 mmol) was dissolved in CH$_2$Cl$_2$ (5 mL) and added to the mixture dropwise. Additional DIEA (0.2 mL) was added to maintain the pH=8. After stirring at 0° C. for three hours, water was added to quench the reaction and the solvent was removed under reduced pressure. The residue was dissolved in EtOAc (50 mL) and washed with sat. NaHCO$_3$ (20 mL), sat. NaCl (2×20 mL), 1N HCl (20 mL), sat. NaCl (3×20 mL), dried over MgSO$_4$, and evaporated to give the title compound in 89% yield (180 mg) as a white solid which was used directly in the next step.

TLC: Rf=0.85 (DCM/MeOH/AcOH=85:10:5)
MS: (M+H)+=376.9

EXAMPLE 7

Preparation of Ethyl 2-(4-benzylsulfonyl-2-oxopiperazino] acetate:

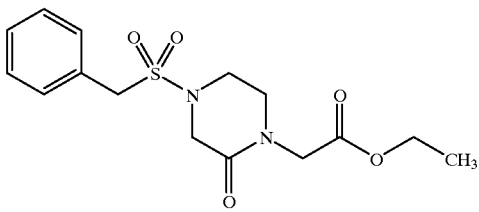

Starting with a-toluenesulfonyl chloride and the compound of Example 5. the title compound was prepared following the procedure of Example 6 as a white solid in 98% yield.

TLC: Rf−0.72 (CH$_2$Cl$_2$/MeOH/AcOH=85:10:5)
MS (M+H)+=341.4

EXAMPLE 8

Preparation of Ethyl 2-{2-oxo-4-[(e)-2-phenyl-1-ethenylsulfonyl]piperazino} acetate:

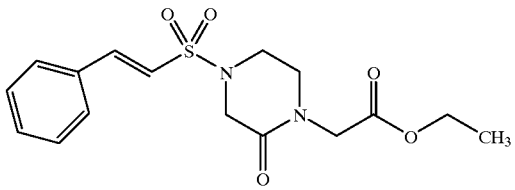

The title compound was prepared as a white solid from trans-βstyrenesulfonyl chloride and the compound of Example 5 by following the procedure analogous to that described in Example 6 which was obtained in 80% yield.

TLC: Rf−0.79 (CH$_2$Cl$_2$/MeOH/AcOH-85:10:5)
MS (M+H)+=353.2

EXAMPLE 9

Preparation of 2-[4-(2-Naphthylsulfonyl)-2-oxopiperazino] acetic acid:

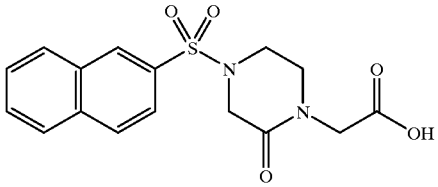

To a solution of the compound of Example 6 (M.W.=376, 130 mg, 0.35 mmol) in 10 mL of EtOH/dioxane (3:1) mixture was added 2 mL 1N LiOH aqueous solution and the reaction mixture was stirred for 2 hours. The solvent was evaporated and the residue was dissolved in water (20 ml). The solution was acidified by adding 1N HCl (2 mL, pH=2) and extracted with EtOAc (2×50 mL). The combined organic extract was washed with sat. NaCl (3×20 mL). dried over MgSO$_4$, evaporated to give the title compound as a white solid in 96% yield.

TLC: Rf=0.27 (CH$_2$Cl$_2$/MeOH/AcOH=85: 10:5)

MS: (M+H)+=348.9

EXAMPLE 10

Preparation of 2-[4-Benzylsulfonyl-2-oxopiperazino] acetic acid:

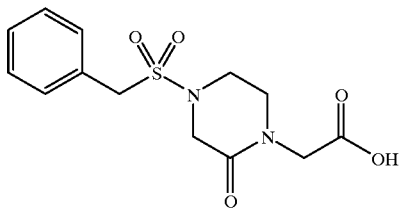

The title compound was prepared from the compound of Example 7 by the same procedure described for Example 9 as white solid in 95% yield.

MS: (M+H)+=313.1

EXAMPLE 11

Preparation of 2-{2-Oxo-4-[(E)-2-phenyl-1-ethenylsulfonyl]piperazino} acetic acid:

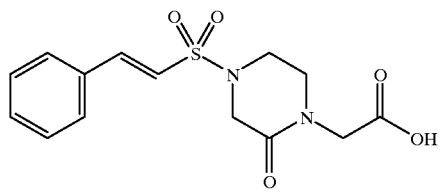

The tide compound was prepared from the compound of Example 8 by the same procedure described in Example 9 as white solid in 98% yield.

MS: (M+H)+=325.1

EXAMPLE 12

Preparation of N1-[(1s)-4-imino(4-methylphenyl-sulfonamido)-methylamino-1-(1,3-thiol-2-ylcarbonyl)-butyl]-2-[4-(2-naphthylsulfonyl)-2-oxopiperazino] acetamide:

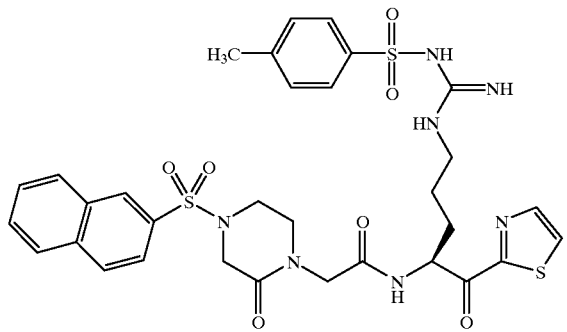

The compound of Example 9 (M.W.=312, 80 mg, 0.23 mmol) and the compound of Example 3 (103 mg, 0.26 mmol) were dissolved in DMF (2 ml) and cooled to 0° C. under argon. DIEA (100 μl) and BOP (120 mg, 0.27 mmol) were added sequentially and the mixture was stirred at 0° C. for 2 hours. The reaction was monitored by RP-HPLC. Upon completion of reaction, the solvent was removed by high vacuum at 30° C. The residue was dissolved in a mixture of EtOAc-H$_2$O (25 mL:5 mL) and the aqueous layer was discarded The organic layer was washed with sat. NaCl (2×10 mL), 1 N HCl (10 mL), sat NaCl (2×10 mL), dried over MgSO$_4$, evaporated to give the tide compound as a white solid (yield 90%) which was carried on directly to the next step.

ES-MS: (M+H)+=726.2

EXAMPLE 13

Preparation of N1-[(1s)-4-imino(4-methylphenyl-sulfonamido)methylamino-1-(1,3-thiazol-2-ylcarbonyl) butyl]-2-(4-benzylsulfonyl-2-oxo-piperazino)acetamide:

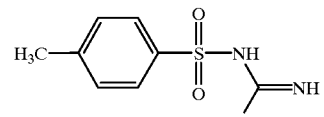
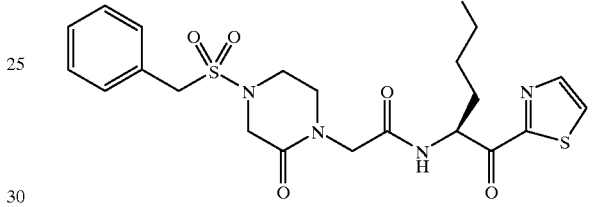

The crude title compound was prepared from the compound of Example 10 and the compound of Example 3 by the same procedure as described in Example 12. Reverse phase HPLC purification gave the title compound in 90% yield as white powder.

MS: (M+H)+=690.1

EXAMPLE 14

Preparation of N1-[(1s)-4-imino(4-methylphenyl-sulfonamido)methylamino-1-(1,3-thiazol-2-ylcarbonyl)-butyl]-2-{2-oxo4-[(E-2-phenyl-1-ethenylsulfonyl]piperazino}-acetamide:

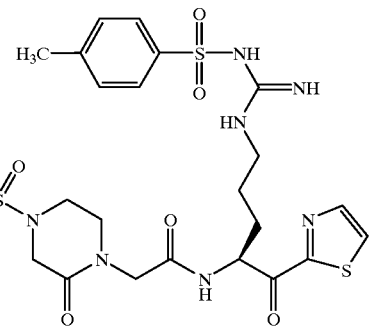

The title compound was prepared from the compound of Example 11 and the compound of Example 3 by the same procedure as described in Example 10, which was obtained in 85% yield as white powder.

MS: (M+H)+=702.2

EXAMPLE 15

Preparation of N1-[(1s)-4-amino(imino)-methylamino-1-(1,3-thiazol-2-ylcarbonyl)butyl]-2-[4-(2-naphthylsulfonyl)-2-oxopiperazino] acetamide (Compound VI(l)):

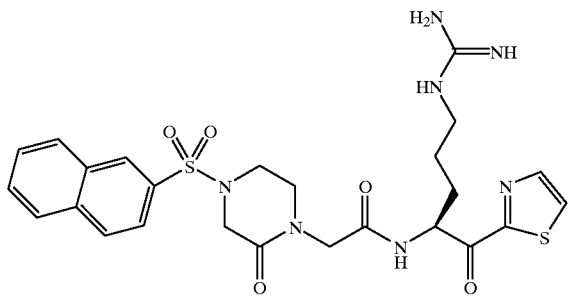

100 mg of the crude compound of Example 12 (0.14 mmol), 1 mL of anisole and 0.25 mL of EtSMe were placed in an HF-cleavage vessel and cooled by liquid $N_2$. 10 mL of HF was condensed into the vessel and the mixture was stirred at —5° C.-0° C. for 1 hour. HF was removed under vacuum to give a gummy residue. The residue was triturated with 20 mL of $Et_2O$ and the solvent was removed by filtration. This was repeated once. The gummy residue was dissolved in 1 mL of 0.1% TFA in MeCN and diluted with 9 mL of 0.1% TFA in $H_2O$. purified by RP-HPLC to give the title compound. as a white power, in a 60% yield.

ES-MS: (M+H)+=572.1

EXAMPLE 16

Preparation of N1-[(1s)-4-amino(imino)-methylamino-1-(1,3-thiazol-2-ylcarbonyl)butyl]-2-(4-benzylsulfonyl-2-oxopiperazino)acetamide (Compound VI(8)):

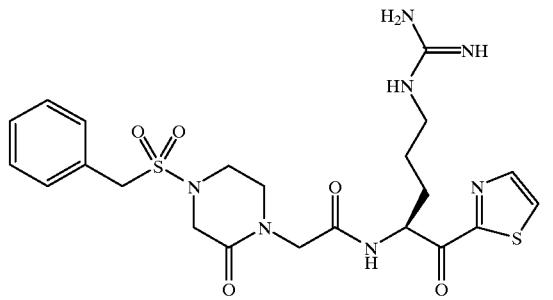

The title compound was prepared from the compound of Example 13 as white powder in 70% yield by the same procedure as described in Example 15.

ES-MS: (M+H)+536.1

EXAMPLE 17

Preparation of N1-[(1s)-4-amino(imino)methyl-amino-1-(1,3-thiazol-2-ylcarbonyl)butyl]-2-{2-oxo-4-(E)-2-phenyl-1-ethylsulfonyl)-2-oxopiperazino] acetamide (Compound VI(7)):

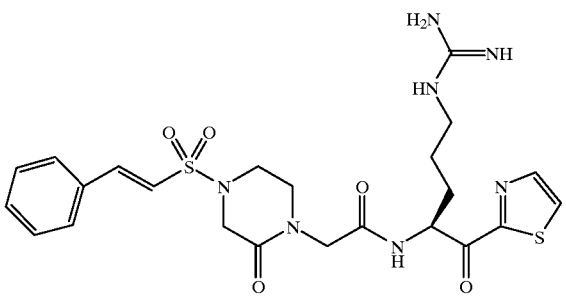

The title compound was prepared from the compound of Example 14 as a white powder in 87% yield by the same procedure as described in Example 15.

ES-MS: (M+H)+=547.8

EXAMPLE 18

Preparation of Ethyl 2-[4-t-butyloxycarbonyl)piperazino) acetate:

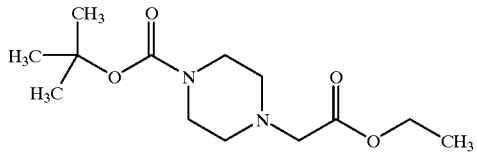

To a solution of N-t-Boc-piperazine (M.W.=186.3, 0.93 g, 5 mmol), ethyl iodoacetate (M.W.=214, 1.07 g, 5 mmol) in DMF (10 mL) was added 0.88 mL of DIEA(0.88 mL, 5 mmol), stirred at 60° C. for 4 hours, then at room temp. over night. The mixture was diluted with EtOAc (150 mL), washed with sat NaCl (30 mLx3), dried over $MgSO_4$ and concentrated. The residue was triturated with ether giving 1.3 g (96% yield) of the title compound as a yellowish crystalline solid.

TLC: Rf=0.76 (EtOAc/MeOH=10:1)

MS: (M+H)+=273.0

EXAMPLE 19

Preparation of Ethyl 2-piperazinoacetate:

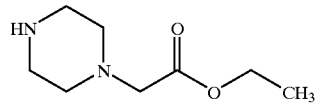

The compound of Example 18 (M.W.=272.3, 300 mg, 1.1 mmol) was treated with 10 mL of 4N HCl in dioxane at 0° C. for 2 hrs. $Et_2O$ was added to the mixture, the white solid was filtered and washed once with $Et_2O$. The solid was dissolved in sat $NaHCO_3$(10 mL), extracted with $CH_2Cl_2$ (20mlx3). The combined organic layers were dried over $MgSO_4$ and evaporated resulting in the title compound as a white solid in 80% yield.

TLC: Rf0.48 (EtOAc/MeOH=10:1)

EXAMPLE 20

Preparation of Ethyl 2-[4-{2-[1-(t-butyloxycarbonyl)-4-piperidyl]ethyl}piperazino) acetate:

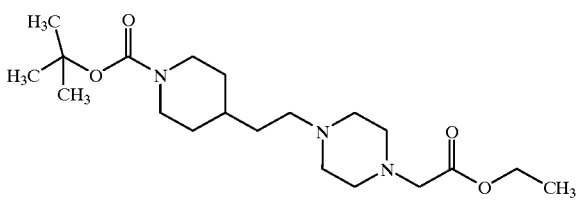

The compound of Example 19 (M.W.=172.2, 80 mg, 0.46 mmol) was dissolved in DMF (2 mL) and cooled to 0° C., DIEA (90 μl, 0.5 mmol) was added to the solution followed by N-Boc4-piperidine ethyl iodide (M.W.=339, 158 mg, 0.47 mmol). The mixture was stirred at room temp. for 3 days. After DMF was removed by high vacuum, the residue was dissolved in 0.1% TFA in H$_2$O and purified by reverse phase HPLC to give 150 mg (85% yield) of the title compound as a white powder.

TLC: Rf=0.19 (EtOAc /MeOHS=10:1)

MS: (M+H)+=384.5

EXAMPLE 21

Preparation of 2-[4-{2-[1-(t-Butyloxycarbonyl)-4piperidyl]ethyl}piperazino)acetic acid:

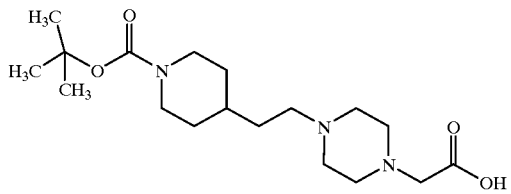

To a solution of the compound of example 20 (M.W.= 383.5, 100 mg, 0.26 mmol) in EtOH (10 mL) was added 1 mL 1N aq. LiOH and stirred at 0° C. for 3 hours. The solution was acidified with 1 mL 1N HCl and solvent was evaporated. The residue was subjected to reverse phase HPLC purification to give the title compound as a white powder in 90% yield.

TLC: Rf=0.10 (ACOEt/MeOH=10:1)

MS: (M+H)+=356.5

EXAMPLE 22

Preparation of tert-Butyl 4-(2-{4-[(1s)-4-imino(4-methylphenylsufonamido) methylamino-1-(1,3-thiazol-2-ylcarbonyl)butylcarbamoylmethyl]piperazino}ethyl)-1-piperidine carboxylate:

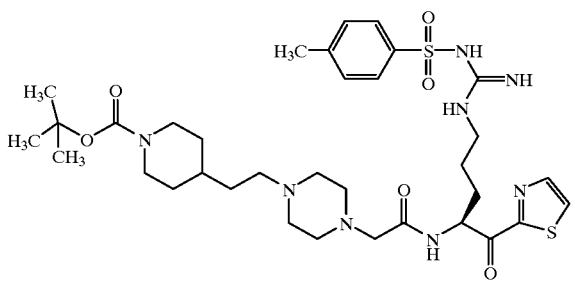

The title compound was prepared from the compounds of Examples 21 and of 3 as a white powder in 91% yield by following the procedure described in Example 12.

MS (M+H)+=547.8

EXAMPLE 23

Preparation of N1-[(1s)-4-amino(imino)methylamino-1-(1,3-thiazol-2-ylcarbonyl)butyl]-2-{4-[2-(4-piperidyl)ethyl]piperazino} acetamide (Compound XVI(1)):

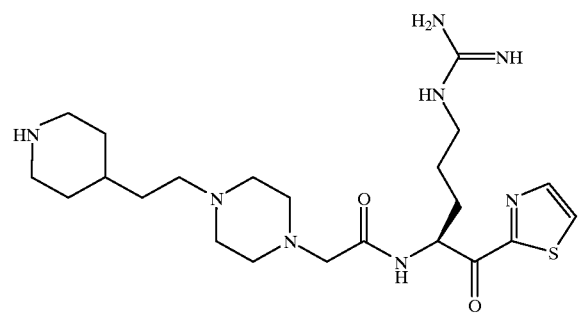

The title compound was prepared from the compound of Example 22 as a white powder in 100% yield by following the procedure described in Example 15.

ES-MS (M+H)+=547.8

EXAMPLE 24

Preparation of Ethyl 2-(7-oxo-4-phenyl-1,4-diazepan-1-yl)acetate:

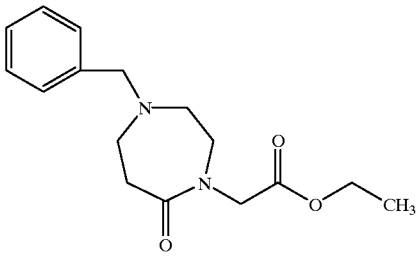

130 mg (0.63 mmol) of 1-benzyl-(1,4)diazepen-5-one was dissolved in 20 ml of anhydrous THF in a ovendried round-bottomed flask, cooled to −78° C. and treated with lithium bis(trimethylsilyl)amide (1 M in THF, 765 μl, 0.75 mmol). The reaction mixture was stirred at −78° C. for 1.5 hours and 114 μl (M.W.=214, 0.95mmol) of ethyl iodoacetate was then added. After stirring at −78° C. for an additional hour, the reaction mixture was allowed to warm to 0° C., quenched by adding 1 ml of 1N HCl, concentrated and then purified directly by reversed phase HPLC(C-18). 120 mg (65% yield ) of ethyl 2-(7-oxo-4-phenyl-1,4-diazepan-1-yl)acetate was obtained as a light yellow powder after lyophilization.

TLC R=0.60 (DCM/MeOH/EtOAc/HOAc=9:3:3:0.5

$^1$H NMR (400MHz, CDCl$_3$) d 7.42(m, 5H), 4.23(d, 2H), 4.16(q, 2H), 1.25(t,3 H), 2.6–4.8(b, 10H)

ES-MS: (M+H)$^+$=291.0

EXAMPLE 25

Preparation of Ethyl 2-(7-oxo-1,4-diazepan-1-yl)acetate:

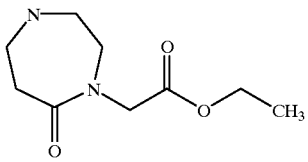

In a 50 ml round-bottomed flask, 70 mg (0.35 mmol) of the compound of Example 24 was dissolved in 15 mL of MeOH. 14 mg of 5% Pd on activated carbon (Degussa type, E101 NO/W) was added to the solution and stirred at room temperature under atmospheric $H_2$ overnight. The catalyst was removed by filtration and filtrate was concentrated to afford ethyl 2-(7-oxo-1,4-diazepan-1-yl)acetate (100% yield). This compound was carried on to the next step without further purification.

TLC Rf=0.16 (DCM/MeOH/EtOAc/HOAc=9:3:3:0.5)

$^1$H NMR (400MHz, $CDCl_3$) d 9.8(b, 1H), 4.13(q, 2H), 4.15(b, 2H), 3.78(b,2H), 3.47(b, 2H), 3.32(b, 2H), 2.97(b, 2H), 1.24(t,3H)

EXAMPLE 26

Preparation of Ethyl 2-(4-benzylsulfonyl-7-oxo-1,4-diazepan-1-yl)acetate:

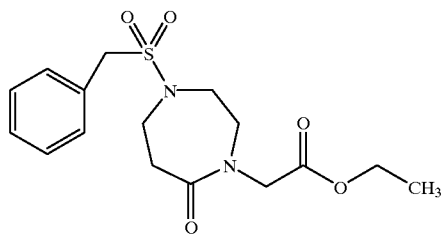

50 mg (0.25mmol) of the compound of Example 25 was dissolved in 7 ml of DCM and cooled to −78° C. 67 mg (0.35mmol) of α-toluenesulfonyl chloride and 41 µl (M.W.= 129.25, d=0.742) of DIEA were then added. After stirring at −78° C. for several minutes, the reaction mixture was allowed to warm to 0° C. in 1 hour. The reaction mixture was concentrated and the residue was dissolved in EtOAc. The organic solution was washed with saturated aqueous $NaHCO_3$. saturated aqueous NaCl and 1 N HCl, dried over $MgSO_4$, concentrated and purified by C18 reversed phase HPLC. Lyphilization gave ethyl 2-(4-benzylsulfonyl-7-oxo-1,4-diazepan-1-yl)acetate as a white powder (56.5% yield).

TLC Rf0.40 (DCM/MeOH/EtOAc/HOAc,=9:3:3:0.5)

$^1$H NMR (400MHz, $CDCl_3$) d 7.5 ( m, 5H), 4.21(s, 2H), 4.16(q,2H), 4.10(s,2H), 4.45(d, 2H), 3.38(d, 2H), 3.26(m, 2H), 2.70(m,2H), 1.25(t,3H)

ES-MS: $(M+H)^+=355.0$

EXAMPLE 27

Preparation of Ethyl 2-(4-benzylsulfonyl-7-oxo-1,4-diazepan-1-yl)acetic acid:

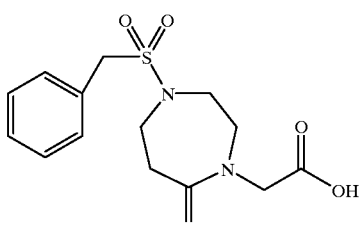

A solution of 5 ml of 0.2N LiOH in $H2O/CH_3CN$ (1:10) was added to 30 mg (0.085 mmol) of the compound of Example 26. After stirring at room temperature for 2 hour, the reaction mixture was acidified with 1N HCl (pH=3), concentrated to about 1 ml, and extracted several times with EtOAc. All EtOAc layers were combined and concentrated to give ethyl 2-(4-benzylsulfonyl-7-oxo-1,4-diazepan-1-yl) acetic acid as white solid.

TLC Rf-0.33 (DCM/MeOH/HOAc=85:10:5)

$^1$H NMR (400MHz, $CDCl_3$) d 7.36 ( m, 5H), 4.23(bs, 2H), 4.13(q,2H), 3.45(m,2H), 3.33(d, 2H), 3.26(t, 2H), 2.70(dd,2H)

ES-MS: $(M+H)^+=326$

EXAMPLE 28

Preparation of N1-[(1S-4-imino(4-methylphenylsulfonamido)methylamino-1-(1,3-thiazol-2-yl)butyl]-2-(4-benzylsulfonyl-7-methylene-1,4-diazepan-1-yl)acetamide:

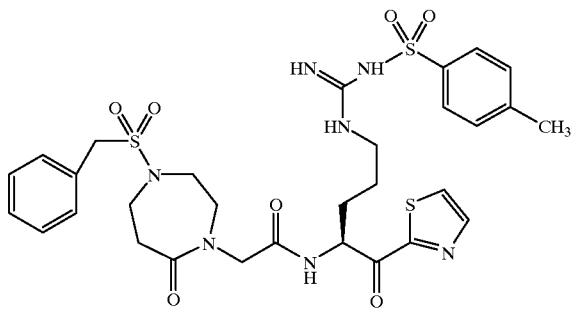

Starting with the acid of Example 27 and the amine of Example 3, the title compound was prepared in 91.0% yield following the procedure described in Example 10.

ES-MS: $(M+H)^+=704$

EXAMPLE 29

Preparation of N1-[(1S)-4-amino(imino)methylamino-1-(1,3-thiazol-2-yl)butyl]-2-(4-benzysulfonyl-7-methylene-1, 4doazepan-1-yl)acetamide (Compound VII(5)):

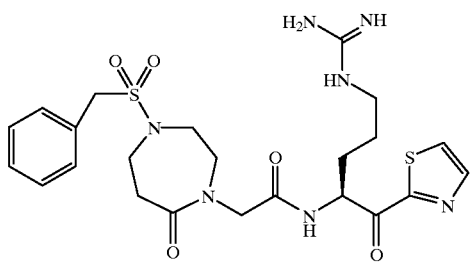

Starting with the compound of Example 28, the title compound was prepared in 100% yield following the procedure described in Example 15.

ES-MS: (M+H)⁺=550.4

EXAMPLE 30

Preparation of Ethyl 2-{2,5-dioxo-4-[2-(4-pyridyl)ethyl]piperazino}acetate:

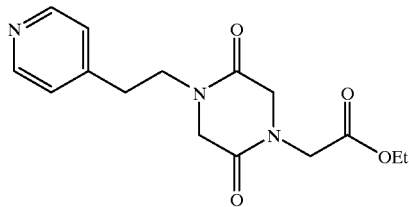

A 25 mL round bottom flask was charged with bromoacetic acid (0.42g, 3.3 mmol), diethyl iminodiacetate (591 µL, 3.0 mmol) and 6 mL of DCM, followed by DCC (0.6809 g, 3.3 mmol). The mixture was stirred at room temperature for about one hour. The white solid DCU was filtered through a glass fritted funnel. The filtrate was concentrated in vacuo and diluted with 4.5 mL dichloromethane, followed by 4-(2-aminoethyl)pyridine (203 µL, 2.0 mmol). The resulting mixture was stirred at room temperature for 18 hour, diluted with DCM and washed with saturated NaHCO₃. The aqueous layer was further extracted with DCM and all the organic layers were combined, dried (MgSO₄), concentrated in vacuo and chromatographed through 80 g of silica gel eluting with 7% methanol in DCM to afford the title compound as a white solid (0.67 g, 74%).

TLC Rf=0.35 (DCM:MeOH=93:7)

HPLC: 8.8 min; $C_{18}$, 0–100% CH₃CN over 25 minutes, 1.5 mL/min.

¹H NMR(400 MHz/CDCl₃) δ8.52 (d, 2H), 7.16 (d, 2H), 4.18 (q, 2H), 4.08 (s, 2H), 4.03 (s, 2H), 3.64 (t, 2H), 2.87 (t, 2H), 1.26 (t, 3H).

¹³C NMR(100 MHz(CDCl₃) δ167.8, 164.0, 163.2, 150.2, 150.1, 146.8, 124.0, 61.8. 51.0, 50.2, 47.1, 46.7, 32.4, 14.1.

ES-MS: (M+H)⁺=306.2

EXAMPLE 31

Preparation of Ethyl 2-(2,5-dioxo-4-benzylpiperazino)acetate:

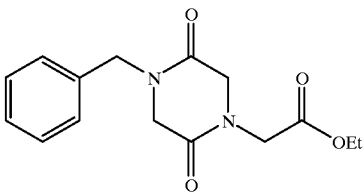

Starting with benzyl amine, the title compound was prepared in 68% yield following the procedure described in Example 30.

HPLC: 11.5 min; $C_{18}$, 0–100% CH₃CN over 25 minutes, 1.5 mL/min.

¹H NMR(400 MHz (CDCl₃) δ7.31–7.19 (m, 5H), 4.56 (s, 2H), 4.17 (q, 2H), 4.13 (s, 2H), 4.09 (s, 2H), 3.87 (s, 2H), 1.23 (t, 3H)

ES-MS: (M+H)⁺=291.0

EXAMPLE 32

Preparation of 2-(4-{2-[1-(tert-Butyloxycarbonyl)-4-piperidyl]ethyl}-2,5-dioxopiperazino)acetic acid:

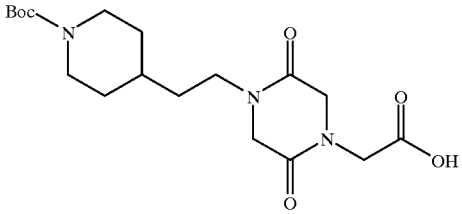

A 10 mL vial was charged with the compound of Example 30 (0.18 g, 0.6 mmol), 6 mL MeOH, di-tert-butyl dicarbonate (0.26 g, 1.2 mmol), 5% Pd on activated carbon (0.1095 g). The mixture was stirred at room temperature under 100 psi of hydrogen for 18 hours. The catalyst was filtered through Celite, concentrated in vacuo, and dissolved in 6 mL acetonitrile. A solution of 1 M LiOH (1.54 mL, 1.5 mmol) was added and stirred at 23° C. for one hour. The acetonitrile was removed by concentrated in vacuo and the resulting crude oil was acidified with 10% citric acid and extracted with ethyl acetate several times. All the organic layers were combined, dried ( MgSO₄), concentrated in vacuo to afford the title compound as a white solid (166 mg, 72%).

HPLC: 13.2 min; $C_{18}$, 0–100% CH₃CN over 25 minutes, 1.5 mL/min.

¹H NMR(400 MHz/CDCl₃) δ8.78 (br. s, 1H), 4.04–3.95 (m, 9H), 3.46 (t, 2H), 2.58 (t, 2H), 1.60 (d, 2H), 1.44–1.30 (m, 2H), 1.35 (s, 9H), 1.08–0.98 (m, 2H)

ES-MS: (M+H)⁺=384.0

EXAMPLE 33

Preparation of 2-(2,5-Dioxo4 benzylpiperazino)acetic acid:

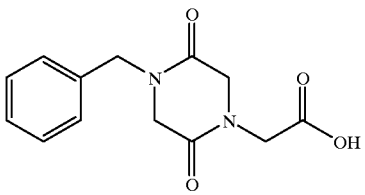

Starting with the compound of Example 31, the title compound was prepared in 69% yield following the saponification procedure described in Example 32 using 1N HCl instead of 10% citric acid for the acidification.

HPLC: 9.9 min; $C_{18}$, 0–100% $CH_3CN$ over 25 minutes, 1.5 mL/min.

$^1$H NMR(400 MHz/$CD_3OD$) δ7.3 6–7.21 (m, 5H). 4.58 (s, 2H), 4.16 (s. 2H), 4.13 (s. 2H), 3.90 (s, 2H)

EXAMPLE 34

Preparation of 2-(4-{2-[1-Carbobenzyloxyamino(imino) methyl-4-piperidyl]ethyl}-2,5-dioxopiperazino)acetic acid:

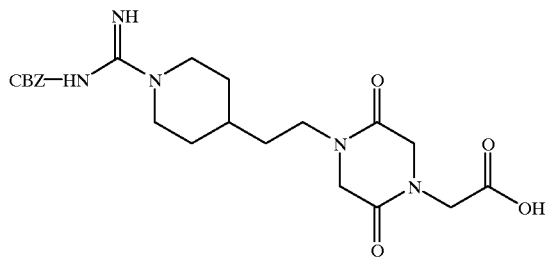

A 25 mL round bottom flask was charged with the compound of Example 30 (0.6642 g, 2.2 mmol), 5 mL MeOH, and 5% Pd on activated carbon (398 mg). The mixture was stirred at room temperature under 120 psi of hydrogen for 60 hours. The catalyst was filtered through Celite and dissolved in 5 mL acetonitrile followed by 1 M LiOH (5.4 mL, 5.4 mmol). The resulted mixture was stirred at 23° C. for one hour. The acetonitrile was removed by concentration in vacuo and the resulting crude oil was acidified with 1N HCl. EtOAc was not able to extract any of the acid out NaHCO₃ was added until the aqueous was basic, followed by N-carbobenzyloxy-carbobenzyloxyimino-methylsulfanyl-methanamine (857 mg, 2.4 mmol), triethylamine (334 mL, 2.4 mmol) and 5 mL acetonitrile. The mixture was refluxed for 18 hours, acidified by 1N HCl and extracted with EtOAc. All the organic layers were combined, dried over MgSO₄, concentrated in vacuo and purified by preparative HPLC to afford the title compound as a white solid (136mg, 14%).

HPLC: 12.9 min; $C_{18}$, 0–100% $CH_3CN$ over 25 minutes, 1.5 mL/min.

$^1$H NMR(400 MHz/$CD_3OD$) δ7.38–7.14 (m, 5H), 5.09 (s, 2H), 4.16–4.06 (m, 8H), 3.42 (t, 2H), 2.78 (br. s, 2H), 1.71 (d, 2H), 1.51–1.43 (m, 3H), 1.16–1.02 (m, 2H)

EXAMPLE 35

Preparation of tert-Butyl 4-(2-(2-{4-[(1S)-4-amino (nitroimino)methyl amino-1-hydroxy(phenethylcarbamoyl) methylbutylcarbamoylmethyl]-2.5-dioxo piperazino}ethyl)-1-piperidinecarboxylate:

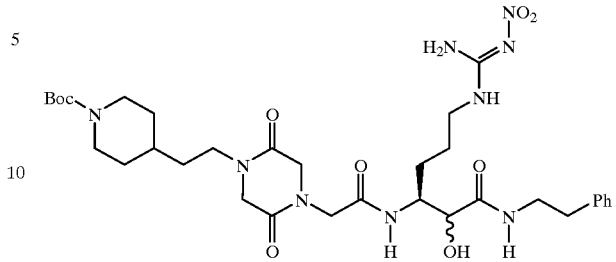

A 25 mL round bottom flask was charged with the compound of Example 32 (68.4 mg, 0.18 mmol), Arg(NO₂)(OH)CONH(CH₂)₂Ph•HCl (76.3 mg, 0.20 mmol), prepared by the method of Webb, T. R et al, WO 94/08941, BOP (86.8 mg, 0.20 mmol) and 4 mL 30% DMF in acetonitrile, followed by DIEA (68 μL, 0.39 mmol). The mixture was stirred at room temperature for 1.5 hours, poured into a separatory fennel and then diluted by ethyl acetate. Satrated NaCl solution, 10% citric acid, and 5% NaHCO₃ were used to wash the reaction mixture, respectively. The organic layer was dried over MgSO₄, concentrated in vacuo and purified by preparative HPLC to afford a white solid (64.9 mg, 51%) after lyophilization HPLC: 14.4 and 14.6 min; $C_{18}$, 0–100% $CH_3CN$ over 25 minutes, 1.5 mL/min.

$^1$H NMR(400 MHz/$CD_3OD$) δ7.24–7.16 (m, 5H), 4.25 (br. s, 1H), 4.14–3.95 (m, 9H), 3.52–3.03 (m, 7H), 2.97–2.61 (m, 4H), 1.72–1.30 (m, 17H), 1.16–1.02 (m, 2H)

ES-MS: (M+H)$^+$=718.3

EXAMPLE 36

Preparation of N1-benzyl-(3S)-6-amino(nitroimino) methylamino-3-(2,5-dioxo-4-benzylpiperazinomethylcarboxamido)-2-hydroxyhexanamide:

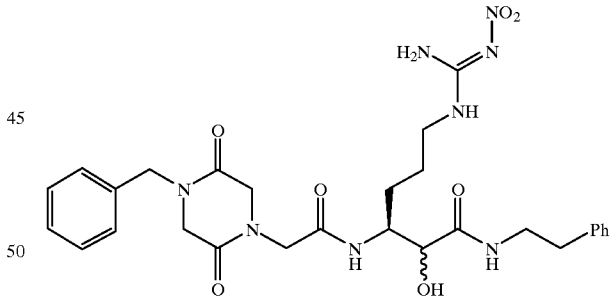

Starting with the compound of Example 33, the title compound was prepared in 35% yield following the procedure described in Example 35.

HPLC: 12.2 and 12.3 min; $C_{18}$, 0–100% $CH_3CN$ over 25 minutes, 1.5 mL/min.

$^1$H NMR(400 MHz/$CD_3OD$) δ7.36–7.16 (m, 10H), 4.81 and 4.79 (two s, 2H), 4.29–4.20 (m, 1H), 4.18–3.86 (m, 8H), 3.51–3.38 (m, 2H), 3.30–3.06 (m, 2H), 2.81–2.74 (m, 2H), 1.69–1.44 (m, 3H)

ES-MS: (M+H)$^+$=597.1

EXAMPLE 37

Preparation of N1-phenethyl-(3S)-6-amino(nitroimino) methylamino-3-(4-{2-[1-carbobenzyloxyamiino(imino)

methyl-4-piperidyl]ethyl}-2,5-dioxopiperazinomethyl-carboxamido)-2-hydroxylhexanamide:

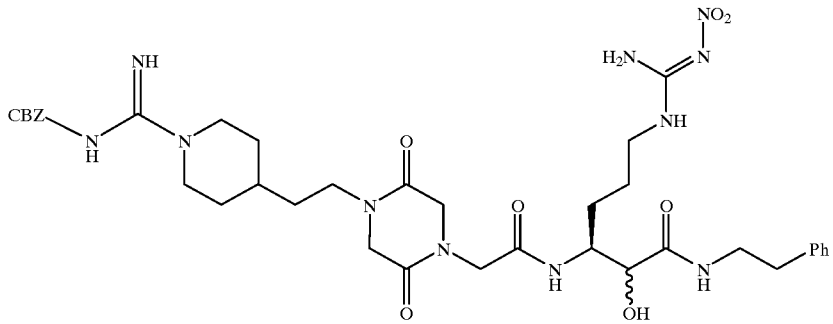

Starting with the compound of Example 34, the title compound was prepared in 51% yield following the procedure described in Example 35.

HPLC: 13.8 and 14.0 min; $C_{18}$, 0–100% $CH_3CN$ over 25 minutes, 1.5 mL/min.

$^1$H NMR(400 MHz/$CD_3OD$) δ7.37–7.08 (m, 10H), 4.27 (br. s, 1H), 4.15–4.01 (m, 10H), 3.53–3.39 (m, 4H), 3.28–3.09 (m, 2H), 2.79 (AB, 2H), 1.80–1.70 (m, 2H), 1.68–1.43 (m, 7H), 1.35–1.7 (m, 1H), 1.16–1.14 (m. 2H)

EXAMPLE 38

Preparation of N1-phenethyl-(3S)-6-amino(imino)methylamino-3-{2.5-dioxo-4-[2-(4-piperidyl)ethyl]piperazinomethylcarboxamido}-2-oxohexanamide (Compound V(10)):

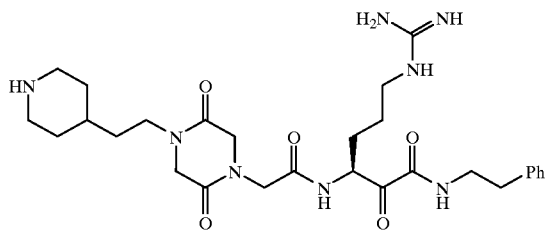

The compound of Example 35 (63.6 mg, 0.09 mmol), 1N HCl (89 μL, 0.09 mmol), 5% Pd on activated carbon (38.2 mg), and 3 mL MeOH were combined and stirred under 50 psi of hydrogen for 18 hours. The catalyst was filtered using a glass fritted funnel and the filtrate was concentrated in vacuo, mixed with 1M TFA in DMSO (133 μL, 0.15 mmol) and 0.5 M IBX in DMSO (886 μL, 0.45 mmol). After stirring at room temperature overnight, the reaction mixture was diluted with 10 mL 0.001N HCl. The solution was chromatographed through a Sepharose SP column using gradient elution from 0.001N HCl to 0.1N HCl to afford the desired HCl salt as a white solid (42.8 mg, 80%) after lyophilization.

HPLC: 9.7 min; $C_{18}$, 0–100% $CH_3CN$ over 25 minutes, 1.5 mL/min.

$^1$H NMR(400 MHz/$D_2O$) δ721–7.03 (m, 5H), 4.01–3.82 (m, 2H), 3.32–3.19 (m, 5H), 2.99–2.20 (m, 3H), 2.27 (t, 2H), 2.65 (t, 2H), 1.80 and 1.76 (two br. s, 3H), 1.47–1.33 (m, 6H), 1.29–1.09 (m, 7H)

ES-MS: (M+W$^+$=571.3

EXAMPLE 39

Preparation of N1-phenethyl-(3S)-6-amino(imino)methylamino-3-(2,5-dioxo-4-benzylpiperazinomethylcarboxmido)-2oxohexanamide (Compound V(9)):

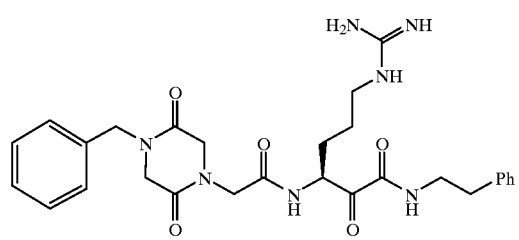

Starting with the compound of Example 36, the title compound was prepared in 50% yield and purified by preparative HPLC following the procedure described in Example 38.

HPLC: 10.9 min; $C_{18}$, 0–100% $CH_3CN$ over 25 minutes, 1.5 mL/min.

ES-MS: (M+H)$^+$=550.0

EXAMPLE 40

Preparation of N1-phenethyl-(3S)-6-amino(imino)methylamino-3-{4-(2-[1-amino(imino)methyl-4-piperidyl]ethyl)-2,5-dioxopiperazinomethylcarboxamido)-2-oxohexanamide (Compound V(11)):

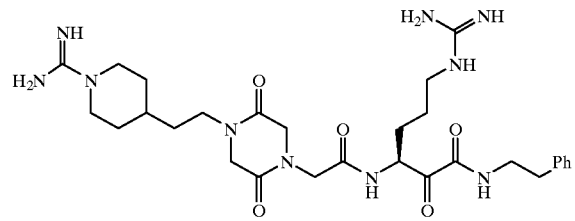

Starting with the compound of Example 37, the title compound was prepared in 68% yield following the procedure described in Example 38.

HPLC: 8.81 min; $C_{18}$, 0–100% $CH_3CN$ over 25 minutes, 1.5 mL/min.

ES-MS: (M+H)$^+$=613

EXAMPLE 41

Preparation of Benzyl 2-[2,5-dioxo-4-(4-pyridinylmethyl)piperazino]acetate:

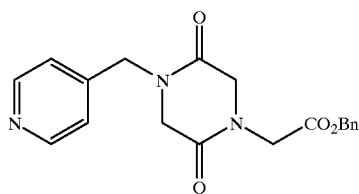

A 2 g sample of hydroxymethylpolystyrene (0.8 mmol equivalents per gram of resin. 1.6 mmol) was washed twice with DCM, then with THF. The washed resin was suspended in 20 mL of THF and 660 mg of bromoacetic acid (4.7 mmol) were added followed by 20 mg of DMAP (0.176 mmol) and 250 μL (4.7 mmol) of DIC. The resin was agitated for 2 hours, filtered, washed twice with THF and the above procedure repeated. The resin was then washed twice with 40 mL of DMF and twice with DCM. The resin was then treated with 20 mL of a 2M solution of 4-aminomethylpyridine (4 mL in 16 mL of DMSO) in DMSO for 18 hours, filtered, and washed successively twice with 40 mL each of DCM, MEOH, and DCM. The acetylation procedure from above was repeated. The resin was then treated with a 1.4 M DMSO solution of glycine benzyl ester (2.3 g in 10 mL of DMSO; prepared by dissolving 3.3 g of the hydrochloride in 10 mL of 10% $Na_2CO_3$, extraction 3 times with ethyl acetate, drying over anhydrous $K_2CO_3$, and concentration). After 18 hours, the filtrate was collected along with a subsequent wash with 10 mL of DMSO and 200 mL of DCM. The combined filtrates were concentrated, dissolved in EtOAc and washed twice with water and twice with 0.2 M phosphate (pH 7). The organic layer was dried ($MgSO_4$) and concentrated to afford 920 mg of an oil which was purified by flash chromatography on silica gel eluting with 5% MeOH/DCM to give 284 mg (50%) of a white solid TLC Rf=0.5 (10% MeOH/DCM)

HPLC: retention time 10.1 min; $C_{18}$, 0–100% $CH_3CN$ over 25 minutes, 1.5 mL/min.

$^1$H-NMR (400-MHz, $CDCl_3$) d 3.94 (s,2), 4.16 (s,2), 4.18 (s,2), 4.59 (s,2), 5.18 (s,2), 7.16 (d,2), 7.35 (n,5), 8.58 (d,2)

ES-MS: $(M+H)^+$=354.1; calculated $(M+H)^+$=354.4

EXAMPLE 42

Preparation of 2-[4-[1-(tert-Butyloxycarbonyl)-4piperidylmethyl]-2,5-dioxopiperazino}acetic acid:

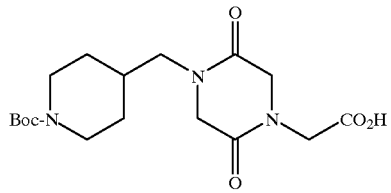

A solution of 442 mg (1.25 mmol) of Example 41, 548 mg (2.5 mmol) of $BOC_2O$. 273 mg of 5% Pd/C (Degussa E101 R/W) in 12.5 mL of MeOH is stirred under a 50 psi of hydrogen gas. After 4 h, the solution is filtered, concentrated, dissolved in EtOAc, and washed twice with brine, dried ($MgSO_4$), and concentrated to give 465 mg of a white solid. Purification by flash chromatography on silica gel eluting with up to 10% MeOH/DCM afforded 201 mg (44%) of the title compound as a white solid.

TLC Rf=0.1 (10% MeOH/DCM)

HPLC: retention time 12.5 min; $C_{18}$, 0–100% $CH_3CN$ over 25 minutes, 1.5 mL/min.

ES-MS: $(M+Na)^+$=392.2; calculated (M+Na)=392.2

EXAMPLE 43

Preparation of tert-Butyl 4-2-(2-(4-[(1S)-4-amino(nitroimino)methylamino-1-hydroxy(phenethylcarbamoyl)methylbutylcarbamoylmethyl]-2,5-dioxopiperazino}ethyl)-1-piperidinecarboxylate:

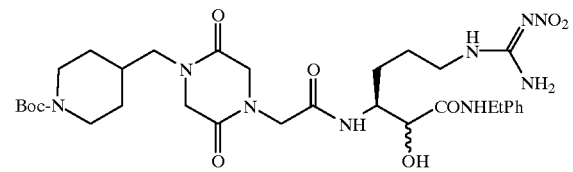

To a solution of the compound from Example 42 (0.12 mmol, 44 mg) in 0.5 mL of DMF was added a solution of $Arg(NO_2)(OH)CONH(CH_2)Ph•TFA$ (59.8 mg, 0.13 mmol; prepared from the Boc protected compound by treatment with 40% TFA/DCM (0.1 M) for 30 min and concentration in vacuo) in 0.5 ml DMF followed by DIEA (103 μl, 0.6 mmol) and BOP (58.3 mg, 0.13 mmol). The solution was allowed to stir for 16 hours. The solvent was removed in vacuo, dissolved in EtOAc (20 mL), and washed with 10% citric acid (25 mL), $H_2O$ (25 ml), 5% $NaHCO_3$ (25 mL) and brine (25 mL). The organic layer was dried over $MgSO_4$ and concentrated in vacuo to afford 56 mg (66%) of an off white solid.

HPLC: 13.4, 13.6 min.; $C_{18}$, 0–100% $CH_3CN$ over 25 min., 1.5 mL/min.

MS: (M+H)=704.5; calculated (M+H)=704.4

EXAMPLE 44

Preparation of N1-phenethyl-(3S)-6-amino(imino)methylamino-3-{2,5-dioxo-4-[2-(4-piperidyl)ethyl]piperazinomethylcarboxamido}-2-oxohexanamide (Compound V(8)):

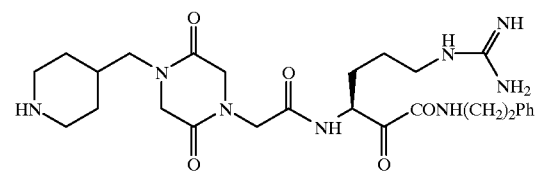

A solution of 50 mg (0.07 mmol) of the compound from Example 43, 50 mg 5% Pd/C (Degussa E101 R/W), and 1N HCl (71 μl, 0.07 mmol) in 2 mL of MeOH is stirred under 50 psi of hydrogen gas. After 16 h, the solution is filtered, concentrated in vacuo, redissolved in 40%TFA/DCM (0.1M) and allowed to stir for 30 min. The solution was then concentrated in vacuo, and crude material was redissolved in 1M TFA in DMSO (10 μl, 1.5eq) and IBX (760 μl, 0.5M in DMSO) and allowed to stir for 15 h. The reaction mixture was dissolved in 1.5 mL 1N HCl and washed with DCM (3×5 mL). The aqueous layer was then purified on a 2.5cm $C_{18}$ column and lyophilized directly to give 9.5 mg (24%) as a fluffy white solid HPLC: 8.6 min; $C_{18}$, 0–100% $CH_3CN$ over 25 min., 1.5 mL/min ES-MS: $(M+H)^+$=557.0; calculated (M+H)=557.3

EXAMPLE 45

(Determination of IC$_{50}$)

The compounds of the present invention are first dissolved in a buffer to give solutions containing concentrations such that assay concentrations range from.0–100 μM. In assays for thrombin, prothrombinase and factor Xa, a synthetic chromogenic substrate would be added to a solution containing a test compound and the enzyme of interest and the residual catalytic activity of that enzyme would then be determined spectrophotometrically.

The IC$_{50}$ of a compound is determined from the substrate turnover. The IC$_{50}$ is the concentration of test compound giving 50% inhibition of the substrate turnover. Preferred compounds of the invention desirably have an IC$_{50}$ of less than 500 nM in the factor Xa assay, preferably less than 200 nM, and more preferably less than 100 nM. Preferred compounds of the invention desirably have an IC$_{50}$ of less than 4.0 μM in the prothrombinase assay, preferably less than 200 nM, and more preferably less than 10 nM. Preferred compounds of the invention desirably have an IC$_{50}$ of greater than 1.0 μM in the thrombin assay, preferably greater than 10.0 μM, and more preferably greater than 100.0 μM.

Amidolytic Assays for determining protease inhibition activity

Factor Xa and thrombin assays are performed at room temperature, in 0.02 M Tris HCl buffer, pH 7.5, containing 0.15 M NaCl. The rates of hydrolysis of the para-nitroanilide substrate S-2765 (Chromogenix) for factor Xa, and the substrate Chromozym TH (Boehringer Mannheim) for thrombin following preincubation of the enzyme with the test compound for 5 minutes at room temperature are determined using a Softmax 96-well plate reader (Molecular Devices), monitored at 405 nm to measure the time dependent appearance of p-nitroanilide.

The prothrombinase inhibition assay is performed in a plasma free system with modifications to the method as described by Sinha, et al., Thromb. Res., 75:427–436 (1994). The activity of the prothrombinase complex is determined by measuring the time course of thrombin generation using the p-nitroanilide substrate Chromozym TH. The assay consists of a 5 minute preincubation of selected compounds to be tested as inhibitors with the complex formed from factor Xa (0.5 nM), factor Va (2 nM), phosphatidyl serine:phosphatidyl choline (25:75, 20 μM) in 20 mM Tris HCl buffer, pH 7.5, containing 0.15 M NaCl, 5 mM CaCl$_2$ and 0.1% bovine serum albumin. Aliquots from the complex-test compound mixture are added to prothrombin (1 nM) and Chromozym TH (0.1 mM). The rate of substrate cleavage is monitored at 405 nm for two minutes. Several concentrations of a given test compound are assayed in duplicate. A standard curve of thrombin generation by an equivalent amount of untreated complex is then used for determination of percent inhibition.

The compounds of the invention exhibited inhibitory activity in the Factor Xa assay described above. Typical IC$_{50}$ values were within the range of 4–500 nM.

EXAMPLE 46

The antithrombotic efficacy of the compounds of this invention can readily be evaluated using a series of studies in rabbits, as described below. These studies are also useful in evaluating a compounds effects on hemostasis and its the hematological parameters.

Antithrombotic Efficacy in a Rabbit Model of Venous Thrombosis

A rabbit deep vein thrombosis model as described by Hollenbach, et al., Thromb. Haemost 71:357–362 (1994), is used to determine the in vivo antithrombotic activity of the compounds of the present invention Rabbits are anesthetized with I.M. injections of Ketamine, Xylazine, and Acepromazine cocktail.

A standard protocol consists of insertion of a thrombogenic cotton thread and copper wire apparatus into the abdominal vena cava of the anesthetized rabbit A nonocclusive thrombus is allowed to develop in the central venous circulation and inhibition of thrombus growth is then used as a measure of the antiombotic activity of the compound being evaluated. Test agents or control salin are administered trough a marginal ear vein catheter. A femoral vein catheter is used for blood sampling prior to and during steady state infusion of the compound being evaluated. Initiation of thrombus formation will begin immediately after advancement of the cotton thread apparatus into the central venous circulation. The compounds being evaluated are administered from time=30 minutes to time=150 minutes at which point the experiment is terminated. The rabbits are euthanized and the thrombus excised by surgical dissection and characterized by weight and histology. Blood samples are then analyzed for changes in hematological and coagulation parameters.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A compound having the formula:

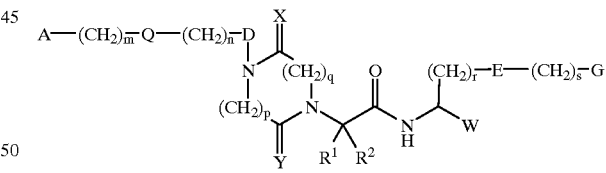

wherein:

R$^1$ is selected from the group consisting of H, C$_{1-6}$alkyl, C$_{3-8}$cycloalkyl, C$_{1-3}$alkylaryl, C$_{1-3}$alkyl-C$_{3-8}$cycloalkyl and aryl and R$^2$ is H, or R$^1$ and R$^2$ are taken together to form a carbocyclic ring;

m is an integer from 0–2;

n is an integer from 0–6;

p is 1;

q is 1;

r is an integer from 0–4;

s is an integer from 0–1;

A is selected from the group consisting of $R^3$, —$NR^3R^4$,

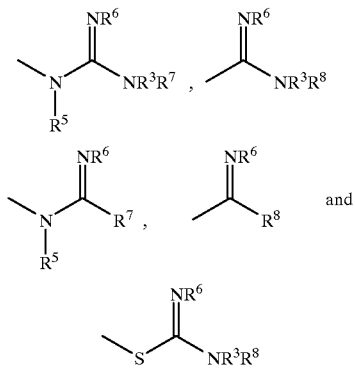

where $R^3$, $R^4$, $R^5$ and $R^6$ are independently selected from the group consisting of H, —OH, $C_{1-6}$alkyl, aryl and $C_{1-4}$alkylaryl; $R^7$ is selected from the group consisting of H, $C_{1-6}$alkyl, aryl and $C_{1-4}$alkylaryl, or can be taken together with $R^5$ or $R^6$ to form a 5–6 membered ring; and $R^8$ is selected from the group consisting of H, $C_{1-6}$alkyl, aryl and $C_{1-4}$alkylaryl, or can be taken together with $R^6$ to form a 5–6 membered ring;

- Q is selected from the group consisting of a direct link, $C_{1-6}$alkyl, $C_{3-8}$cycloalkyl, $C_{2-6}$alkenyl, $C_{2-6}$alkenylaryl, aryl, and a five to ten membered heterocyclic ring system containing 1–4 heteroatoms selected from the group consisting of N, O and S;
- D is selected from the group consisting of a direct link, —CO—, —$SO_2$—, —DECO—, —$NR^9$—$SO_2$— and —$NR^9$—CO—, where $R^9$ is selected from the group consisting of H, —OH, $C_{1-6}$alkyl, aryl and $C_{1-4}$alkylaryl;
- E is selected from the group consisting of a direct link, $C_{3-8}$-cycloalkyl, aryl, and a five to ten membered heterocyclic ring system containing 1–4 heteroatoms selected from the group consisting of N, O and S;
- G is selected from the group consisting of $R^{10}$, —$NR^{10}R^{11}$,

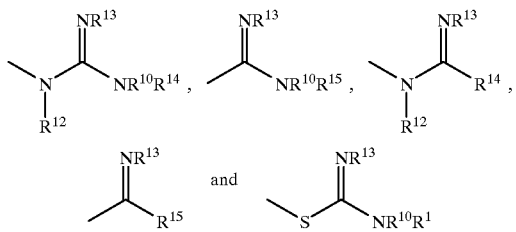

where $R^{10}$, $R^{11}$, $R^{12}$ and $R^{13}$ are independently selected from the group consisting of H, —OH, $C_{1-6}$alkyl, aryl and $C_{1-4}$alkylaryl; $R^{14}$ is selected from the group consisting of H, $C_{1-6}$alkyl, aryl and $C_{1-4}$alkylaryl, or can be taken together with $R_{12}$ or $R^{13}$ to form a 5–6 membered ring; and $R^{15}$ is selected from the group consisting of H, $C_{1-6}$alkyl, aryl and $C_{1-4}$alkylaryl, or can be taken together with $R^{13}$ to form a 5–6 membered ring; with the proviso that when G is $R^{10}$, then E must contain at least one N atom;

X and Y are independently selected from the group consisting of O and $H_2$;

W is selected from the group consisting of H,

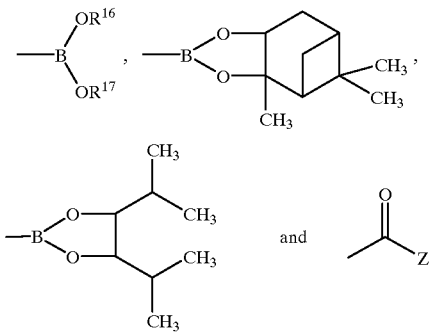

where $R^{16}$ and $R^{17}$ are independently selected from the group consisting of H, $C_{1-3}$alkyl and aryl; anti Z is selected from the group consisting of H, —$COOR^{18}$, —$CONR^{18}R^{19}$, —$CF_3$, —$CF_2CF_3$ and a group having the formula:

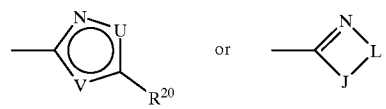

where:
- $R^{18}$ and $R^{19}$ are independently selected from the group consisting of H, $C_{1-6}$alkyl, aryl and $C_{1-4}$alkylaryl;
- U is selected from the group consisting of —O—, —S—, —N— and —NH—; and
- V is selected from the group consisting of —O—, —S—, —N— and —NH—; with the proviso that at least one of U or V is —N— or —NH—;
- $R^{20}$ is selected from the group consisting of H, $C_{1-6}$alkyl, $C_{2-6}$alkenyl, $C_{0-6}$alkylaryl, $C_{2-6}$alkenylaryl, $C_{0-6}$alkylheterocyclo, $C_{2-6}$alkenylheterocyclo, —$CF_3$ and —$CF_2CF_3$;
- J is selected from the group consisting of —S—, —SO—, —$SO_2$—, —O— and —$NR^{21}$—, where $R^{21}$ is selected from the group consisting of H, $C_{1-6}$alkyl and benzyl; and
- L is selected from the group consisting of:

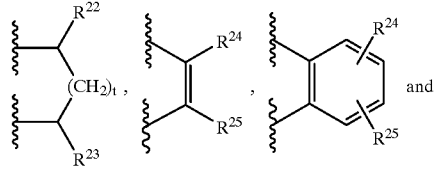

a $C_{6-10}$ heterocyclic ring system substituted by $R^{24}$ and $R^{25}$ and containing 1–4 heteroatoms selected from N, S and O;
  where t is an integer from 0–2;
  $R^{22}$ and $R^{23}$ are independently selected from the group consisting of H, $C_{1-6}$alkyl, aryl, $C_{1-6}$alkylaryl, —$COOR^{26}$, —$CONR^{26}R^{27}$, —CN and —$CF_3$;
  $R^{24}$ and $R^{25}$ are independently selected from the group consisting of H, $C_{1-6}$alkyl, aryl, $C_{1-6}$alkylaryl, $C_{1-4}$alkyloxy, halogen, —$NO_2$, —$NR^{26}R^{27}$, —$NR^{26}COR^{27}$, —$OR^{26}$, —$OCOR^{26}$, —$COOR^{26}$, —$CONR^{26}R^{27}$, —CN, —$CF_3$, —$SO_2NR^{26}R^{27}$ and $C_{1-6}$alkyl-$OR^{26}$; and

73

$R^{26}$ and $R^{27}$ are independently selected from the group consisting of H, $C_{1-6}$alkyl, $C_{1-3}$alkylaryl and aryl; and all pharmaceutically acceptable salts and optical isomers thereof.

2. A pharmaceutical composition for treating a condition in a mammal characterized by undesired thrombosis comprising a pharmaceutically acceptable carrier and the compound of claim 1.

3. A method for treating a condition in a mammal characterized by undesired thrombosis comprising administering to said mammal a therapeutically effective amount of the compound of claim 1.

4. The method of claim 3, wherein the condition is selected from the group consisting of: unstable angina, refractory angina, myocardial infarction, transient ischemic attacks, thrombotic stroke, embolic stroke, disseminated intravascular coagulation, septic shock, deep venous thrombosis, pulmonary embolism, reocclusion or restenosis of reperfused coronary arteries.

5. A method for inhibiting the coagulation of biological samples, comprising the administration of the compound having the formula:

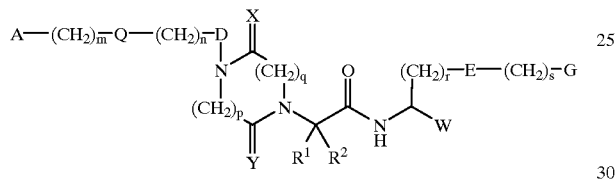

wherein:

$R^1$ is selected from the group consisting of H, $C_{1-6}$alkyl, $C_{3-8}$cycloalkyl, $C_{1-3}$alkylaryl, $C_{1-3}$alkyl-$C_{3-8}$cycloalkyl and a and $R^2$ is H, or $R^1$ and $R^2$ are taken together to form a carbocyclic ring;

m is an integer from 0–2:

n is an integer firm 0–6;

p is 1;

g is 1;

r is an integer from 0–4;

s is an integer from 0–1:

A is selected from the group consisting of $R^3$, —$NR^3R^4$.

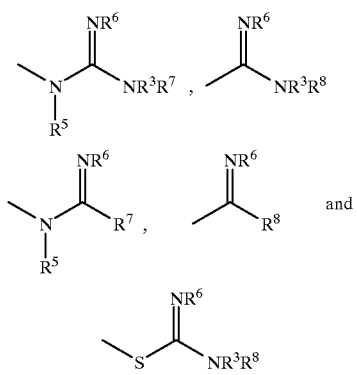

where $R^3$, $R^4$, $R^5$ and $R^6$ are independently selected from the group consisting of H, —OH, $C_{1-6}$alkyl, aryl and $C_{1-4}$alkylaryl: $R^7$ is selected from the group consisting of H, $C_{1-6}$alkyl, aryl and $C_{1-4}$alkylaryl, or can be taken together with $R^5$ or $R^6$ to form a 5–6 membered ring: and $R^8$ is selected from the group consisting of H, $C_{1-6}$alkyl, aryl and

74

$C_{1-4}$alkylaryl, or can be taken together with $R^6$ to form a 5–6 membered ring:

Q is selected from the group consisting of a direct link, $C_{1-6}$alkyl, $C_{3-8}$cycloakyl, $C_{2-6}$alkenyl, $C_{2-6}$alkenyl, aryl, and a five to ten membered heterocyclic ring system containing 1–4 heteroatoms selected from the group consisting of N, O and S:

D is selected from the group consisting of a direct link, —CO—, —$SO_2$—. —O—CO—, —$NR^9$—$SO_2$— and —$NR^9$—CO—, where $R^9$ is selected from the group consisting of H, —OH, $C_{1-6}$alkyl, aryl and $C_{1-4}$alkylaryl;

E is selected from the group consisting of a direct link, $C_{3-8}$cycloakyl, aryl, and a five to ten membered heterocyclic ring system containing 1–4 heteroatoms selected from the group consisting of N, O and S:

G is selected from the group consisting of $R^{10}$, —$NR^{10}R^{11}$,

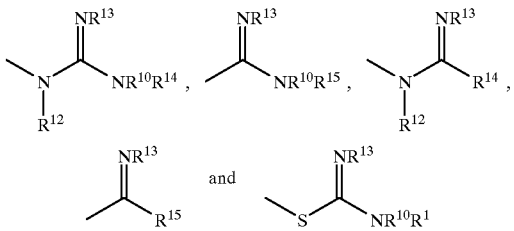

where $R^{10}$, $R^{11}$, $R^{12}$ and $R^{13}$ are independently selected from the group consisting of H, —OH, $C_{1-6}$alkyl, aryl and $C_{1-4}$alkylaryl: $R^{14}$ is selected from the group consisting of H, $C_{1-6}$alkyl, aryl and $C_{1-4}$alkylaryl, or can be taken together with $R^{12}$ or $R^{13}$ to form a 5–6 membered ring: and $R^{15}$ is selected from the group consisting of H, $C_{1-6}$alkyl, aryl and $C_{1-4}$alkylaryl, or can be taken together with $R^{13}$ to form a 5–6 membered ring; with the proviso that when G is $R^{10}$, then E must contain at least one N atom;

X and Y are independently selected from the group consisting of and $H_2$;

W is selected from the group consisting of H,

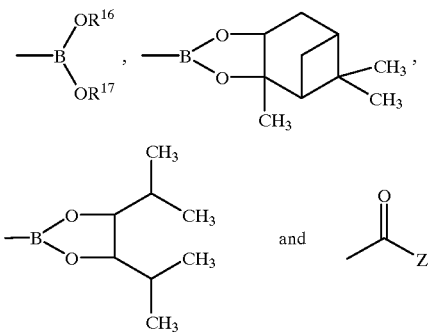

where $R^{16}$ and $R^{17}$ are independently selected from the group consisting of H, $C_{1-3}$alkyl and aryl; and Z is selected from the group consisting of H, —$COOR^{18}$, —$CONR^{18}R^{19}$, —$CF_3$, —$CF_2CF_3$ and a group having the formula:

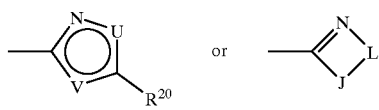

where:

R[18] and R[19] are independently selected from the group consisting of H, $C_{1-6}$alkyl, aryl and $C_{1-4}$alkylaryl, U is selected from the group consisting of —O—, —S—, —N— and —NH—: and V is selected from the group consisting of —O—, —S—, —N— and —NH—; with the proviso that at least one of U or V is —N— or —NH—;

R[20] is selected from the group consisting of H, $C_{1-6}$alkyl, $C_{2-6}$alkenyl, $C_{0-6}$alkylaryl, $C_{2-6}$alkenylaryl, $C_{0-6}$alkylheterocyclo, $C_{2-6}$alkenylheterocyclo, —CF$_2$ and —CF$_2$CF$_2$;

J is selected from the group consisting of —S—, —SO—, —SO$_2$—, —O— and —NR[21]— where R[21] is selected from the group consisting of H, $C_{1-6}$alkyl and benzyl; and L is selected from the group consisting of:

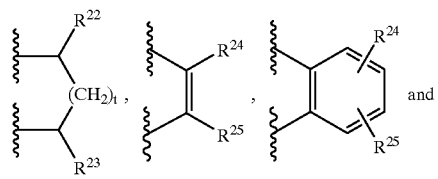

a $C_{6-10}$-heterocyclic ring system substituted by R[24] and R[25] and containing 1–4 heteroatoms selected from N, S and O;

where t is an integer from 0–2;

R[22] and R[23] are independently selected from the group consisting of H, $C_{1-6}$alkyl, aryl, $C_{1-6}$alkylaryl, —COOR[26], —CONR[26]R[27], —CN and —CF$_3$;

R[24] and R[25] are independently selected from the group consisting of H, $C_{1-6}$alkyl, aryl, $C_{1-6}$alkylaryl, $C_{1-4}$alkyloxy, halogen, —NO$_2$, —NR[26]R[27], —NR[26]COR[27], —OR[26], —OCOR[26], —COOR[26], —CONR[26]R[27], —CN, —CF, —SO$_2$NR[26]R[27] and $C_{1-6}$alkyl-OR[26]; and R[26] and R[27] are independently selected from the group consisting of H, $C_{1-6}$alkyl, $C_{1-3}$alkylaryl and aryl:

and all pharmaceutically acceptable salts and optical isomers thereof.

6. A compound having the formula:

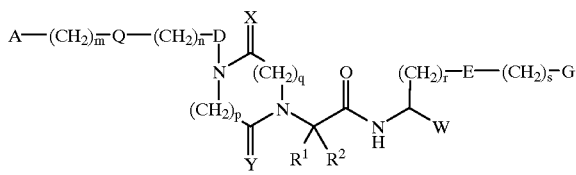

wherein:

R[1] is H;
R[2] is H;
m is 0;
n is 1;
p is 1;
q is 1;
r is 3;
s is 0;
A is H;
Q is phenyl;
D is —SO$_2$—;
E is a direct link;
G is

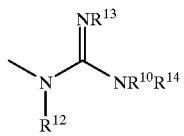

where R[10], R[12], R[13], and R[14] are each H;
X is H$_2$;
Y is O;
W is

where Z is

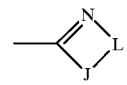

where:

J is —S—; and
L is

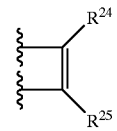

R[24] and R[25] are each H; and all pharmaceutically acceptable salts and optical isomers thereof.

7. A pharmaceutical composition for treating a condition in a mammal characterized by undesired thrombosis comprising a pharmaceutically acceptable carrier and the compound of claim 6.

8. A method for treating a condition in a mammal characterized by undesired thrombosis comprising administering to said mammal a therapeutically effective amount of the compound of claim 6.

9. The method of claim 8, wherein the condition is selected from the group consisting of: unstable angina, refractory angina, myocardial infarction, transient ischemic attacks, thrombotic stroke, embolic stroke, disseminated intravascular coagulation, septic shock, deep venous thrombosis, pulmonary embolism, reocclusion or restenosis of reperfused coronary arteries.

10. A method for inhibiting the coagulation of biological samples, comprising the administration of the compound of claim 6.

11. A compound of claim 1, wherein:
$R^1$ is H or $C_{1-6}$alkyl;
$R^2$ is H;
m is an integer from 0–1;
n is an integer from 0–4;
r is an integer from 0–4;
s is 0;
$R^3$, $R^4$, $R^5$ and $R^6$ are independently selected from the group consisting of H and $C_{1-6}$alkyl; $R^7$ is selected from the group consisting of H and $C_{1-6}$alkyl, or can be taken together with $R^5$ or $R^6$ to form a 5–6 membered ring; and
$R^8$ is H, $C_{1-6}$alkyl, or can be taken together with $R^6$ to form a 5–6 membered ring;
Q is selected from the group consisting of a direct link, $C_{1-6}$alkyl, $C_{3-8}$cycloalkyl, aryl, and a five to ten membered heterocyclic ring system containing 1–4 heteroatoms selected from the group consisting of N, O and S;
D is selected from the group consisting of a direct link, —CO—, and —SO$_2$—;
E is a direct link;
$R^{10}$, $R^{11}$, $R^{12}$ and $R^{13}$ are independently selected from the group consisting of H and $C_{1-6}$alkyl;
X is $H_2$;
Y is O;
W is selected from the group consisting of:

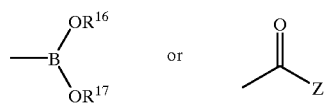

where $R^{16}$ and $R^{17}$ are each H; and Z is selected from the group consisting of H, —COOR$^{18}$, —CONR$^{18}$R$^{19}$, and a group having the formula:

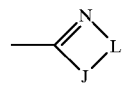

where $R^{13}$ is H, $C_{1-6}$alkyl, or $C_{1-4}$alkylaryl;
$R^{19}$ is $C_{1-4}$alkylaryl;
J is —S—, —O— or —NR$^{21}$ where $R^{21}$ is H or methyl; and
L is selected from the group consisting of:

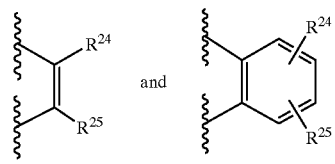

where $R^{24}$ and $R^{25}$ are independently selected from the group consisting of H, —OR$^{26}$, —COOR$^{26}$, —CONR$^{26}$R$^{27}$, and —CF$_3$; and all pharmaceutically acceptable salts and optical isomers thereof.

12. A compound of claim 11, wherein:
$R^1$ is H or methyl;
m is 0;
$R^3$, $R^4$, $R^5$, $R^6$, $R^7$ and $R^8$ are independently H or methyl;
Q is selected from the group consisting of $C_{1-4}$alkyl, aryl, and a five to ten membered heterocyclic ring system containing 1–4 heteroatoms selected from the group consisting of N, O and S;
$R^{10}$, $R^{11}$, $R^{12}$ and $R^{13}$ are independently H or methyl;
$R^{21}$ is H; and
L is

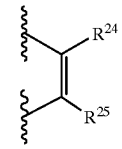

where $R^{24}$ and $R^{25}$ are each H; and all pharmaceutically acceptable salts and optical isomers thereof.

13. A compound of claim 12, wherein $R^1$ is H.
14. A compound of claim 1, wherein:
$R^1$ and $R^2$ are each H;
m is 0;
s is 0;
Y is O; and
W is —C(O)—Z.
15. A compound of claim 14, wherein X is $H_2$.
16. A compound of claim 15, wherein:
r is 3;
D is —SO$_2$—;
E is a bond; and
G is

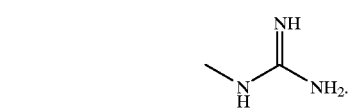

17. A pharmaceutical composition for treating a condition in a mammal characterized by undesired thrombosis comprising a pharmaceutically acceptable carrier and the compound of claim 11.

18. A method for treating a condition in a mammal characterized by undesired thrombosis comprising administering to said mammal a therapeutically effective amount of the compound of claim 11.

19. The method of claim 18, wherein the condition is selected from the group consisting of: unstable angina, refractory angina, myocardial infarction, transient ischemic attacks, thrombotic stroke, embolic stroke, disseminated intravascular coagulation, septic shock, deep venous thrombosis, pulmonary embolism, reocclusion or restenosis of reperfused coronary arteries.

20. A method for inhibiting the coagulation of biological samples, comprising the administration of the compound of claim 11.

* * * * *